(12) United States Patent
Chukwu

(10) Patent No.: US 12,422,397 B1
(45) Date of Patent: Sep. 23, 2025

(54) METHODS AND DEVICES FOR COVID-19 TESTING USING URINE SAMPLES

(71) Applicant: Uchenna Chukwu, Minneapolis, MN (US)

(72) Inventor: Uchenna Chukwu, Minneapolis, MN (US)

(*) Notice: Subject to any disclaimer, the term of this patent is extended or adjusted under 35 U.S.C. 154(b) by 0 days.

(21) Appl. No.: 18/593,648

(22) Filed: Mar. 1, 2024

Related U.S. Application Data

(63) Continuation of application No. 17/897,187, filed on Aug. 28, 2022, now Pat. No. 11,921,076, which is a continuation-in-part of application No. 17/681,839, filed on Feb. 27, 2022.

(60) Provisional application No. 63/154,805, filed on Feb. 28, 2021.

(51) Int. Cl.
*G01N 27/333* (2006.01)
*G01N 33/493* (2006.01)

(52) U.S. Cl.
CPC ......... *G01N 27/333* (2013.01); *G01N 33/493* (2013.01)

(58) Field of Classification Search
None
See application file for complete search history.

(56) References Cited

U.S. PATENT DOCUMENTS 11,629,387 B1 * 4/2023 Chukwu ............ G01N 33/5308
435/5

OTHER PUBLICATIONS

Relevant prosecution history of sibling U.S. Appl. No. 17/897,187, now U.S. Pat. No. 11,921,076.
Relevant prosecution history of sibling U.S. Appl. No. 17/845,031, now U.S. Pat. No. 11,629,387.
Relevant prosecution history of parent U.S. Appl. No. 17/681,839, pending.

* cited by examiner

*Primary Examiner* — J. Christopher Ball

(57) ABSTRACT

The present invention generally includes methods, devices and/or kits for the detection of a COVID-19 infection in an individual by measuring the level or concentration or one or more ions present in a urine sample that is substantially free of COVID-19 RNA, antibodies, or antigen material.

18 Claims, 11 Drawing Sheets

FIGURE 12

| Normal Ion Urine Levels | Day 1 | Day 2 | Day 3 | Day 4 | Day 5 | Day 6 | Day 7 | Day 8 | Day 9 | Day 10 | Day 11 | Day 12 | Day 13 | Day 14 | Day 15 |
|---|---|---|---|---|---|---|---|---|---|---|---|---|---|---|---|
| Sodium (mEq/L) | 91.18 | 208.91 | 154.11 | 163.67 | 112.73 | 136.35 | 96.19 | 189.08 | 43.71 | 152.12 | 49.92 | 164.18 | 58.02 | 162.88 | 194.53 |
| Potassium (mEq per 24 hour) | 29.25 | 62.47 | 62.27 | 39.50 | 29.51 | 117.86 | 105.15 | 59.23 | 58.28 | 25.56 | 81.18 | 53.10 | 41.11 | 70.10 | 95.73 |
| Calcium (mg/24-hour) | 211.81 | 149.84 | 190.05 | 134.47 | 220.57 | 206.76 | 200.63 | 183.69 | 198.22 | 163.52 | 155.97 | 112.13 | 1578.41 | 177.55 | 211.74 |
| Chloride (mEq/L/24 hour) | 129.79 | 213.04 | 223.22 | 139.27 | 177.36 | 161.14 | 179.67 | 207.13 | 245.52 | 191.80 | 213.72 | 198.75 | 239.65 | 198.22 | 137.23 |
| Magnesium (mg/24 hours) | 171.22 | 223.73 | 122.46 | 78.38 | 215.31 | 154.16 | 167.26 | 262.31 | 140.91 | 244.84 | 220.83 | 117.88 | 169.45 | 106.59 | 129.32 |
| pH values | 6.87 | 6.42 | 6.50 | 6.74 | 7.48 | 7.84 | 7.10 | 7.46 | 7.77 | 5.10 | 6.67 | 5.25 | 5.75 | 6.33 | 6.23 |
| Creatinine (mg per 24-hours) | 2085 | 700 | 2688 | 2925 | 2820 | 1631 | 2186 | 1714 | 2795 | 1619 | 1485 | 1671 | 1985 | 1012 | 634 |
| Temp | 98.06 | 97.12 | 98.01 | 97.76 | 97.96 | 98.19 | 97.53 | 97.21 | 97.78 | 98.47 | 97.45 | 97.8 | 97.33 | 97.83 | 97.54 |
| Blood Pressure (mm Hg: Diastolic | 73.3 | 78.9 | 71 | 78.2 | 75.4 | 77.2 | 71.4 | 78.1 | 75.7 | 77.9 | 79.2 | 73.3 | 78.7 | 74.1 | 80.3 |
| Blood Pressure (mm Hg: Systolic) | 116.6 | 111 | 123.7 | 123.4 | 120.5 | 141.4 | 128 | 124.6 | 120.8 | 135.1 | 126.5 | 134.2 | 137.1 | 136.9 | 118.5 |

FIGURE 13

| Normal Ion Urine Levels | Day 16 | Day 17 | Day 18 | Day 19 | Day 20 | Day 21 | Day 22 | Day 23 | Day 24 | Day 25 | Day 26 | Day 27 | Day 28 | Day 29 | Day 30 | Day 31 |
|---|---|---|---|---|---|---|---|---|---|---|---|---|---|---|---|---|
| Sodium (mEq/L) | 214.08 | 138.82 | 103.00 | 102.35 | 215.82 | 143.02 | 141.25 | 88.07 | 154.50 | 88.00 | 109.70 | 205.95 | 146.25 | 210.85 | 170.65 | 20.1 |
| Potassium (mEq per 24 hour) | 33.81 | 100.49 | 50.74 | 28.46 | 34.18 | 54.90 | 84.89 | 97.85 | 124.90 | 64.56 | 66.58 | 107.22 | 37.57 | 114.96 | 116.83 | 39.17 |
| Calcium (mg/24-hour) | 173.58 | 113.15 | 208.47 | 149.83 | 126.16 | 249.47 | 147.13 | 129.38 | 123.82 | 131.93 | 148.77 | 132.91 | 203.12 | 100.95 | 224.75 | 103.02 |
| Chloride (mEq/L/24 hour) | 213.82 | 196.32 | 133.06 | 157.12 | 226.70 | 155.82 | 137.52 | 248.19 | 225.98 | 156.60 | 200.54 | 130.74 | 193.65 | 238.68 | 224.53 | 235.99 |
| Magnesium (mg/24 hours) | 246.84 | 103.65 | 117.10 | 243.99 | 229.09 | 265.25 | 234.24 | 64.59 | 56.61 | 69.61 | 237.66 | 147.22 | 206.22 | 140.19 | 172.22 | 89.8 |
| pH values | 6.74 | 4.90 | 7.29 | 7.44 | 6.45 | 7.63 | 6.70 | 7.68 | 5.19 | 6.85 | 6.70 | 6.28 | 5.79 | 4.97 | 7.7 | 6.24 |
| Creatinine (mg per 24-hours) | 2746 | 1655 | 2431 | 1831 | 1369 | 2293 | 2517 | 2139 | 2232 | 2838 | 515 | 1698 | 1460 | 2080 | 2274 | 636 |
| Temp | 98.78 | 98.7 | 97.3 | 98.9 | 98.8 | 97.6 | 98.1 | 98.7 | 98.22 | 98.81 | 98.59 | 98.13 | 97.22 | 98.94 | 97.05 | 98.93 |
| Blood Pressure (mm Hg: Diastolic | 78.6 | 80.5 | 75.6 | 78.4 | 79.2 | 71.9 | 78.3 | 73.6 | 70.5 | 70 | 73.9 | 73.9 | 75.6 | 72.7 | 74.9 | 72.4 |
| Blood Pressure (mm Hg: Systolic) | 123.5 | 133 | 116.4 | 127.1 | 140.4 | 133.1 | 136.6 | 143.4 | 129.9 | 115.1 | 122.3 | 125.3 | 134.2 | 143 | 141 | 127.3 |

FIGURE 14

| COVID-19 Infection | Day 1 | Day 2 | Day 3 | Day 4 | Day 5 | Day 6 | Day 7 | Day 8 | Day 9 | Day 10 | Day 11 | Day 12 | Day 13 | Day 14 | Day 15 |
|---|---|---|---|---|---|---|---|---|---|---|---|---|---|---|---|
| Sodium (mEq/L) | 16.79 | 8.96 | 4.77 | 19.15 | 14.53 | 1.28 | 0.57 | 8.74 | 15.21 | 2.11 | 13.12 | 19.56 | 13.73 | 10.57 | 1.32 |
| Potassium (mEq per 24 hour) | 19.6 | 13.8 | 17.7 | 14.8 | 12.8 | 15 | 14.8 | 15.4 | 11 | 17.9 | 13.3 | 15.9 | 17 | 15.7 | 11.3 |
| Calcium (mg/24-hour) | 94.6 | 107.6 | 57 | 110.4 | 109.9 | 146.1 | 69 | 136.8 | 108.8 | 77.6 | 87.8 | 142.8 | 79.2 | 135.9 | 98.7 |
| Chloride (mEq/L/24 hour) | 423 | 321 | 374 | 438 | 408 | 354 | 489 | 251 | 481 | 431 | 283 | 267 | 323 | 297 | 335 |
| Magnesium (mg/24 hours) | 274 | 295 | 290 | 272 | 271 | 277 | 274 | 273 | 294 | 287 | 292 | 275 | 273 | 290 | 281 |
| pH values | 5.42 | 5.78 | 6.67 | 4.77 | 6.74 | 6.13 | 4.83 | 6.05 | 4.97 | 6.21 | 4.52 | 4.85 | 6.65 | 5.19 | 6.5 |
| Temp | 104.5 | 100.6 | 101.2 | 99.6 | 102 | 101.6 | 101 | 99.1 | 103.9 | 101.1 | 101.8 | 102.6 | 104.7 | 103.9 | 101.8 |
| Blood Pressure (mm Hg: Diastolic) | 88.1 | 102.9 | 115.5 | 111.9 | 82.4 | 86.4 | 87 | 115.8 | 114.5 | 104.4 | 90.9 | 100.1 | 92.9 | 103.7 | 87.5 |
| Blood Pressure (mm Hg: Systolic) | 151.3 | 154.3 | 148.1 | 158.8 | 158.5 | 150.8 | 147.8 | 152 | 150.3 | 146.4 | 150.1 | 144.5 | 157.4 | 156.1 | 153.8 |

FIGURE 15

| Days | Potassium (mEq per 24 hour) | Sodium (mEq/L) | Chloride (mEq/L/24 hour) | Calcium (mg/24-hour) | Magnesium (mg/24 hours) | Temp (degrees F) | pH | Systolic_BP (mm Hg) | Diastolic_BP (mm Hg) | COVID-19_Prediction |
|---|---|---|---|---|---|---|---|---|---|---|
| 1 | 94 | 97 | 205 | 157 | 124 | 97.1 | 5.7 | 121 | 73 | 0 |
| 2 | 77 | 56 | 194 | 118 | 222 | 97.5 | 7.9 | 138 | 75 | 0 |
| 3 | 26 | 189 | 130 | 175 | 126 | 98.7 | 5.2 | 122 | 72 | 0 |
| 4 | 74 | 145 | 136 | 194 | 234 | 98 | 7.3 | 122 | 78 | 0 |
| 5 | 28 | 205 | 162 | 235 | 238 | 97.1 | 6.3 | 113 | 76 | 0 |
| 6 | 47 | 162 | 235 | 134 | 127 | 97.9 | 6.2 | 132 | 72 | 0 |
| 7 | 15 | 13.6 | 285 | 69 | 277 | 103.9 | 5.8 | 155 | 89 | 1 |
| 8 | 18 | 9.1 | 349 | 95 | 276 | 102.3 | 6.1 | 149 | 106 | 1 |
| 9 | 19 | 6 | 314 | 64 | 280 | 104.9 | 4.6 | 158 | 117 | 1 |
| 10 | 10 | 14.1 | 342 | 133 | 270 | 99.8 | 5.3 | 147 | 84 | 1 |
| 11 | 12 | 12 | 213 | 120 | 274 | 99.3 | 6.1 | 145 | 108 | 1 |
| 12 | 11 | 6 | 252 | 115 | 275 | 99 | 5.9 | 144 | 89 | 1 |
| 13 | 18 | 19 | 303 | 129 | 286 | 101.6 | 4.6 | 159 | 103 | 1 |
| 14 | 18 | 15 | 288 | 81 | 296 | 102.1 | 5.9 | 155 | 96 | 1 |
| 15 | 11 | 8.1 | 227 | 140 | 291 | 101.7 | 4.6 | 154 | 86 | 1 |
| 16 | 18 | 8.1 | 273 | 98 | 295 | 100.5 | 6.7 | 149 | 111 | 1 |
| 17 | 10 | 1.6 | 316 | 112 | 281 | 102.5 | 6.3 | 157 | 87 | 1 |
| 18 | 19 | 16.4 | 200 | 51 | 293 | 100.8 | 6.8 | 148 | 92 | 1 |
| 19 | 12 | 12 | 346 | 78 | 280 | 100 | 6.9 | 156 | 110 | 1 |
| 20 | 15 | 8.3 | 234 | 90 | 280 | 100.3 | 4.9 | 159 | 92 | 1 |
| 21 | 15 | 13.4 | 274 | 75 | 299 | 99.7 | 6.8 | 144 | 87 | 1 |
| 22 | 14 | 2.1 | 377 | 127 | 288 | 100.4 | 6.6 | 148 | 107 | 1 |
| 23 | 52 | 150 | 229 | 155 | 178 | 98.2 | 5.6 | 118 | 73 | 0 |
| 24 | 112 | 77 | 247 | 117 | 247 | 97.6 | 6.4 | 127 | 72 | 0 |
| 25 | 123 | 100 | 163 | 217 | 70 | 98.1 | 5.7 | 123 | 72 | 0 |
| 26 | 92 | 134 | 157 | 209 | 208 | 97.5 | 7.2 | 142 | 78 | 0 |
| 27 | 26 | 68 | 194 | 236 | 155 | 98.8 | 4.7 | 134 | 74 | 0 |
| 28 | 87 | 124 | 235 | 138 | 116 | 97.6 | 6.1 | 136 | 73 | 0 |
| 29 | 60 | 204 | 212 | 241 | 218 | 98.5 | 6.9 | 136 | 70 | 0 |
| 30 | 48 | 203 | 220 | 169 | 145 | 98.4 | 7.7 | 132 | 73 | 0 |
| 31 | 76 | 195 | 213 | 187 | 183 | 98.6 | 5.1 | 118 | 79 | 0 |

METHODS AND DEVICES FOR COVID-19 TESTING USING URINE SAMPLES

CROSS-REFERENCE TO RELATED APPLICATIONS

This application is a continuation application that claims priority to a continuation-in-part application Ser. No. 17/897,187, filed on Aug. 28, 2022, now U.S. Pat. No. 11,921,706, which claims priority to U.S. non provisional patent application Ser. No. 17/681,839, filed on Feb. 27, 2022, which claims priority to U.S. provisional application No. 63/154,805, filed on Feb. 28, 2021, each of which are incorporated herein by reference in their entirety.

BACKGROUND OF THE INVENTION

The present invention generally relates to detecting COVID-19 infections. More specifically, the present invention relates to analyzing one or more urine samples to detect the onset of a COVID-19 infection without having to use SARS-CoV-2 virus, or viral material, and/or antibodies produced in response to a COVID-19 infection. The present invention further includes methods of detecting and/or diagnosing COVID-19 infection by measuring and/or quantifying changes to mineral or ionic levels in a urine sample. Furthermore, the present invention includes devices, test strips, test materials, and/or kits useful in the detection of at least one mineral and/or ionic level in a urine sample.

Coronavirus disease 2019, hereinafter referred to as "COVID-19", is a viral contagious disease caused by severe acute respiratory syndrome coronavirus 2 hereinafter referred to as "SARS-CoV-2". Symptoms of COVID-19 are variable and may begin one to fourteen days after exposure to the virus. Around one in five infected individuals do not develop any symptoms, while other individuals can also spread the virus as early as two days before manifestation of any symptom. In general, people remain infectious for up to ten days in moderate cases, and around two weeks in severe cases.

Various testing methods have been developed to diagnose a COVID-19 infection even before the onset of symptoms. Standard methods include real-time reverse transcription polymerase chain reaction, antigen, and blood tests. Samples can be obtained by various methods, including a nasopharyngeal swab, sputum (coughed up material), throat swabs, deep airway material collected via suction catheter or saliva with the goal at detecting the presence of viral RNA fragments. Results are generally available within a few hours to several weeks although delays have been reported due to overwhelming demand for testing, lack of test reagents, etc. Spit tests are deemed easier than using swabs, which allows for at-home testing even though saliva generally has less RNA material needed for effective detection. Sensitivity from molecular testing typically ranges from 68% to 100%, while the specificity ranges from 92% to 100%. Antigen test sensitivity and specificity are typically lower than molecular techniques. In all cases, test performance data in both asymptomatic and symptomatic persons are limited. People without symptoms can pass on SARS-CoV-2 but estimating their contribution to outbreaks is challenging due in part to the inability to distinguish between people who are asymptomatic and pre-symptomatic.

Ion selectivity in the presence of other, and sometimes competing, ions remain challenging and can result in less accurate detection and/or measurement. For example, sodium ions are similar to potassium ions, therefore, selectivity of either ion in the presence of the other remains challenging.

SUMMARY OF THE INVENTION

The present invention generally includes methods, strips, materials, devices, probes, and/or kits for the detection of a COVID-19 infection in an individual by measuring the level or concentration or one or more ions present in a urine sample without having to use RNA, one or more antibodies, or one or more antigen material.

BRIEF DESCRIPTION OF DRAWINGS

FIG. 12 is TABLE 1A: NORMAL URINARY ION VALUES: DAYS 1 TO DAY 15.

FIG. 13 is TABLE 1B: NORMAL URINARY ION VALUES: DAY 16 TO 31.

FIG. 14 is TABLE 1-COVID 19 INFECTION OR ILLNESS URINARY ION VALUES.

FIG. 15 is TABLE 3: EXAMPLE DATASET USED TO TRAIN MACHINE LEARNING AND DEEP LEARNING MODEL TO PREDICT COVID-19 STATUS.

DETAILED DESCRIPTION OF THE INVENTION

Figure 1:
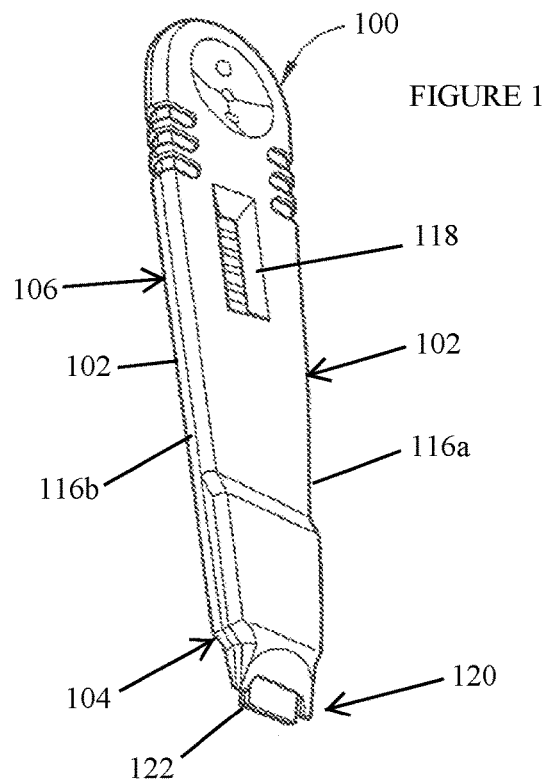
FIG. 1 is a perspective view of a testing device in accordance with a first embodiment of the present invention.

As used herein, the term "asymptomatic" refers to an infected individual who never develops and/or demonstrates COVID-19 symptoms throughout the course of a COVID-19 infection or illness.

As used herein, the term "pre-symptomatic" refers to an infected individual who develops and/or demonstrates mild symptoms before developing and/or demonstrating more severe symptoms. Furthermore, the term "pre-symptomatic" as used herein generally refers to an infected individual who initially does not develop and/or demonstrate COVID-19 symptoms but goes on to develop and/or demonstrate COVID-19 symptoms after a period of time.

As used herein, the term "antigen" refers to a part of a pathogen that elicits an immune response.

As used herein, the term "antibody" generally refers to a large, Y-shaped protein used by an immune system to identify and neutralize one or more foreign object(s), such as one or more pathogenic bacteria and virus(es). Furthermore, the term 'antibody" as used herein refers to one or more proteins that help fight off one or more infections and can provide protection against getting the infection again. Additionally, the term "antibody" as used herein generally refers to one or more immunoglobulin(s) (lg) used by an immune system to identify and neutralize one or more foreign object(s) that gain access to a body.

As used herein, the term "colorimetric analysis" refers to a method of determining a concentration of an element, an ion, a chemical, a compound, a chemical element, chemical compound, or any combination thereof, in a solution with the aid of a color reagent. Furthermore, the term "colorimetric analysis" as used herein may also refer to a technique used to determine a concentration of one or more colored elements, ions, chemical elements, chemical compounds, compound(s), or any combination thereof, in a solution, mixture, or suspension. Additionally, the terms "colorimetry" and "colorimetric analysis" will be used interchangeably throughout the present invention.

As used herein, the term "sensitivity" refers to an ability of a test to correctly identify and/or classify one or more individual(s) with a disease. Additionally, the term "sensitivity" is meant to encompass how often a test can correctly generate a positive result for one or more individual(s) who have the condition that is being tested for in accordance with the present invention. Furthermore, the term "sensitivity" encompasses a percentage or proportion of samples that have a condition. In an example, a test with a 90% sensitivity will correctly return a positive result or classification for 90% of the tested population who have a disease and will return a negative result for 10% of the tested population who have the disease and should have tested positive.

As used herein, the term "true positive rate" refers to a proportion of one or more individual(s) with a known positive condition for which a test result for the one or more individual(s) is positive.

As used herein, the term "true negative rate" refers to a proportion of one or more individual(s) with a known negative condition for which the test result for the one or more individual(s) is negative.

As used herein, the term "specificity refers to an efficacy and/or effectiveness of a test to correctly identify or classify or confer a negative status to one or more tested individual (s) who do not have the condition being tested. For example, a test with a 90% specificity will correctly return a negative result for 90% of the tested population who do not have the condition for which the population is being tested and will return a positive result for 10% of the tested population who do not have the disease and should have tested negative.

As used herein, the term "selectivity of a reaction" generally refers to a ratio of an amount of desired product formed (typically in moles) to an amount of an undesired product formed (typically in moles).

As used herein, the term "machine learning sensitivity" generally refers to the proportion of actual positive cases that are correctly predicted by a machine learning algorithm and/or model. In addition, the term "machine learning sensitivity" as used herein generally refers to a metric that evaluates an ability of a machine learning model or algorithm to correctly predict true positives of each available category. Furthermore, the term "machine learning sensitivity" is meant to encompass a proportion of actual positive cases that are predicted as positive (or true positive) in the present invention. In one example, "machine learning sensitivity" measures the proportion or probability of actual positive cases that got predicted correctly by a machine learning model or algorithm.

As used herein, the term "machine learning specificity" generally refers to a proportion of actual negative cases that were correctly predicted by a machine learning algorithm or model. In addition, the term "machine learning specificity" generally refers to a metric that is effective to evaluate a machine learning model or algorithm's ability to correctly predict true negatives of each available category. Furthermore, the term "machine learning specificity" typically characterizes a proportion of actual negatives that were correctly predicted as negative (or true negative) in the present invention. For example, the "machine learning specificity" measures the proportion or probability of actual negative cases that were predicted correctly by a machine learning algorithm or model.

As used herein, the term "accuracy" generally refers to the numerical proportion or probability of a true positive result or status no matter if the result or status is positive or negative within a selected population.

As used herein, the term "false positive" generally refers to an error in a binary classification in which a test result incorrectly indicates the presence of a condition, such as a disease when the condition (or disease) is not present. Furthermore, the term "false positive" as used herein generally refers to a result that indicates a given condition exists when the given condition does not. In addition, the term "false positive" may be used interchangeably with the term "false positive error" in the present invention.

As used herein, the term "false negative" generally refers to an error in a binary classification in which a test incorrectly fails to indicate the presence of a condition, such as a disease when the condition (or disease) is present. Furthermore, the term "false negative" as used herein, generally refers to a test result which wrongly indicates that a condition does not exist then the condition is present. In addition, the term "false negative" may be used interchangeably with the term "false negative error" in the present invention.

As used herein, the term "hypokalemia" generally refers to a low level or concentration of potassium in the blood serum of a person or an individual and can be measured by a blood potassium test or a serum potassium test. By "low" is meant potassium concentrations or levels generally less than about or below about 3.5 millimoles ("mmol")/Liter ("L"), less than about 3.0 mmol/L, and/or less than about 2.5 mmol/L in the present invention. Furthermore, the term "hypokalemia" is meant to encompass a decrease in blood serum potassium concentration or level to a value that is below the normal range of serum potassium levels, such as less than about 3.5 milliequivalents per liter (mEq/L), less than about 3.0 mEq/L, less than about 2.5 mEq/L, and/or less than about 2.0 mEq/L in the present invention.

As used herein, the term "hyperkalemia" generally refers to a high level or concentration of potassium in the blood serum of a person or individual and can be measured by a blood potassium test or a serum potassium test. By "high" is meant potassium levels or concentrations generally more than about 5.0 mmol/L (or 5 mEq/L), more than about 5.1 mmol/L (or 5.1 mEq/L), and/or more than about 5.2 mmol/L (or about 5.2 mEq/L) of blood serum in the present invention. Furthermore, the term "hyperkalemia" is meant to encompass an increase in serum potassium level or concentration to more than the normal blood serum potassium levels, such as to more than about 5.0 mEq/L (or 5.0 mmol/L), more than about 5.1 mEq/L (or 5.1 mmol/L), more than about 5.2 Eq/L (or 5.2 mmol/L), and/or more than about 5.3 mEq/L (or 5.3 mmol/L).

As used herein, the term "hyponatremia" generally refers to a low level or concentration of sodium in the blood serum of a person or individual and can be measured by a sodium blood test or a serum sodium test. By "low" is meant blood sodium concentrations or levels of less than about 140 mEq/L (or about 140 mmol/L), less than about 136 mEq/L (or about 136 mmol/L), less than about 135 mEq/L (or about 135 mmol/L), and/or less than about 130 mEq/L (or about 130 mmol/L). Furthermore, the term "hyponatremia" is meant to encompass a decrease in serum sodium concentration to less than about 136 mEq/L (or about 136 mmol/L), less than about 135 mEq/L (or about 135 mmol/L), less than about 130 mmol/L (or about 130 mEq/L), and/or less than about 125 mEq/L (or about 125 mmol/L).

As used herein, the term "hypernatremia" generally refers to a serum sodium concentration of more than about 145 mEq/L (or about 145 mmol/L), more than about 146 mEq/L (or about 146 mmol/L), more than about 147 mEq/L (or about 147 mmol/L), and/or more than about 150 mEq/L (or about 150 mmol/L). Furthermore, the term "hypernatremia" is meant to encompass an increase in sodium level or concentration in blood to more than about 145 mEq/L (or 145 mmol/L), more than about 146 mEq/L (or 146 mmol/L), more than about 147 mEq/L (or 147 mmol/L), and/or more than about 150 mEq/L (or 150 mmol/L) in the present invention.

As used herein, the term "hypercalcemia" generally refers to a total blood calcium level in blood serum that is greater than a normal total blood calcium level range of about 2.1 to about 2.6 mmol/L (or about 8.5 to about 10.7 milligrams per deciliter (mg/dL)), or about 4.3 to about 5.2 mEq/L). For example, a total blood serum calcium level or concentration of more than about 2.6 mmol/L (or about 5.2 mEq/L) is generally characterized as hypercalcemia as the normal total blood calcium level range is about 2.1 to about 2.6 mmol/L in an adult. In another example, the total blood calcium is more than about 10.7 mg/dl, more than about 10.8, and/or more than about 10.9 mg/dL. In another example, an ionized calcium concentration or level of more than about 5.4 mg/dl, more than about 5.5 mg/dL, more than about 5.6 mg/dL, and/or more than about 5.7 mg/dl indicates hypercalcemia. In another example, a diagnosis of hypercalcemia occurred when the ionized calcium was more than about 1.30 mmol/L. Furthermore, the term "hypercalcemia" is meant to encompass an increase in total blood serum calcium level or concentration to above the normal range for total blood calcium level to more than about 2.65 mmol/L (or 5.3 mEq/L), more than about 2.7 mmol/L (or 5.4 mEq/L), more than about 2.75 mmol/L (or 5.5 mEq/L), more than about 2.8 mmol/L (or 5.6 mEq/L).

As used herein, the term "hypocalcemia" generally refers to a total serum calcium concentration of less than about 8.8 mg/dL (or less than about 2.20 mmol/L), less than about 8.7 mg/dL, less than about 8.6 mg/dl and/or less than about 8.5 mg/dl in the presence of a normal plasma protein concentration. In addition, the term "hypocalcemia" is meant to include a serum ionized calcium concentration of less than about 4.7 mg/dl (or less than about 1.15 mmol/L), less than about 4.6 mg/dL, less than about 4.5 mg/dL, or less than about 4.4 mg/dL. Furthermore, the term "hypocalcemia" is meant to encompass a decrease in total blood serum calcium level or concentration to below the normal range for total blood calcium level of less than about 2.20 mmol/L, less than about 2.1 mmol/L, less than about 2.0 mmol/L, less than about 1.9 mmol/L in the presence of normal plasma protein concentrations.

As used herein, the term "total calcium test" generally refers to measurement or quantification of both free ionized calcium and bound calcium, such as for example calcium bound to protein in a sample.

As used herein, the term "ionized calcium test" generally refers to measurement or quantification of only free calcium in a sample.

As used herein, the term "hypermagnesemia" refers to a high level of magnesium in blood serum. In general, normal blood magnesium levels is about 1.3 to about 2.1 mEq/L or 0.65-1.05 mmol/L (SI units) in an adult, about 1.4 to about 1.7 mEq/L in children, or about 1.4 to about 2 mEq/L in newborn children. As such, hypermagnesemia is indicated when blood (serum) levels of magnesium exceed 3 mEq per liter with variations occurring due to reporting from different laboratories. For example, hypermagnesemia is diagnosed when concentrations of magnesium are greater than about 1.1 mmol/L in blood serum are reported.

As used herein, the term "hypomagnesemia" generally refers to when blood levels of magnesium drop to or are below about 0.5 mEq per liter and can be measured by blood magnesium or serum magnesium test with variations occurring due to reporting from different laboratories. While not wanting to be bound to theory, it is to be understood that a normal loss of magnesium ions in urine is about 51 to about 269 mg per day based on a 24-hour collection for individuals between about 18 and about 83 years of age. In one example, urinary magnesium levels of more than about 24 mg/day based on a 24-hour collection may indicate a hypomagnesemia status. In another example, hypomagnesemia status is indicated due to losing more than about 50 mg magnesium per 24-hour timeframe in urine. In a third example, a status of hypomagnesemia is indicated by a 24-hour urine magnesium of more than about 24 mg/day or fractional excretion of more than about 0.5% based on 24-hour urine collections.

As used herein, the term "serum" generally refers to the fluid or liquid that remains after blood has clotted.

As used herein, the term "plasma" generally refers to the liquid or fluid that remains when clotting is prevented with the addition of an anticoagulant.

As used herein, the term "interlaboratory variation" generally refers to different laboratories performing the same assay and obtaining statistically different results on the same sample.

In addition, it is to be understood that reference ranges for serum and/or total blood mineral, ion, or any combination thereof concentrations or levels will vary by age and sex and laboratory when practicing the present invention.

As used herein, the term "urine output" or "urine volume excreted" is the volume of urine produced by a human body in a day and may be assessed with the amount of urine produced over a 24-hour timeframe. In general, the normal range of urine output is about 500 to about 2,000 milliliters per day based on a normal fluid intake of about 2 liters per day. However, different laboratories may use report or use slightly different values. Other examples of urine output include more than about 0.5 mL per kg body weight per hour for an adult; more than about 1 ml per kg body weight per hour for a child; and more than about 2 mL per kg body weight per hour for a neonate or baby that is less than about 1 year old.

As used herein, the term 'hypercalciuria' generally refers urinary excretion of more than about 20 to about 250 mg of calcium per day in women, more than about 20 to about 275 mg of calcium per day in men, or more than about 4 mg per kg body weight per day while consuming a regular unrestricted diet. Furthermore, the term "hypercalciuria" is meant to include any level of urine calcium that exceeds net intestinal absorption in a human that leads to a net loss of calcium when practicing the present invention. For example, a urinary excretion of more than about 200 mg of calcium per liter in a urine sample is believed to indicate hypercalciuria. In addition, the term "hypercalciuria" as used herein in meant to include excess calcium in urine in the present invention as demonstrated by having more than about 220 to about 2100 mg calcium per g creatinine. In another example, hypercalciuria is indicated when more than about 350 mg of calcium is excreted over a 24-hour time frame by a human.

As used herein, the term "hypocalciuria" generally refers to a low level of calcium in the urine. By "low" is meant about 50 to about 150 mg/day of calcium in urine (from a diet that is low in calcium) as measured by urinalysis (calcium) or Urinary Ca+2. In general, normal volumes of urine collected over a 24-hour period typically includes about 100 (15 mmol) to about 250 (20 mmol) mg calcium. When a diet is low in calcium consumption, normal urine volumes collected over a 24-hour time period generally includes about 50 to about 150 mg calcium and may drop to about 5 to about 40 mg calcium. As the present invention includes spot urine analysis, calcium may also be reported out as mg calcium per gram creatinine as this metric is not affected by urine volume.

As used herein, the term "low urinary chloride" generally refers to a low level of chloride in the urine. Typically, the normal range of chloride in urine is about 110 to about 250 mEq per day for a 24-hour urine collection although other ranges have been reported. For example, normal values for urinary chloride ranges from about 140 to about 250 mEq/L for a 24-hour urine sample. In another example, a random sample of urine includes normal ranges from about 20 to about 40 mEq/L (or about 20 to about 40 mmol/L) urinary chloride when measuring urinary chloride levels. in an example, the term "low urinary chloride" is meant to include less than about 20 millimoles per liter or milliequivalents per liter urine with some labs varying in their definition of a normal range when using a urine chloride test. Results may be given in milliequivalents per liter (mEq/L) or millimoles per liter (mmol/L).

As used herein, the term "high urinary (or urine) chloride" is meant urine chloride levels of more than the normal range of about 110 to about 250 mEq per day for a 24-hour urine collection. In one example, a level of about 40 mEq/L (40 mmol/L) indicates "high urinary chloride" levels. In another example, "high urinary chloride" generally contains more than a normal range of about 140 to about 250 mEq/L for a 24-hour urine sample. In another example, "high urinary chloride" refers to an amount greater than 140 mEq/L urine over a 24 hour urine collection.

As used herein, the term "high urinary (or urine) sodium" is meant urine sodium levels of more than about 40 mEq/L (40 mmol/L) indicates high urinary sodium levels. In another example, urinary sodium levels are considered high when values are more than about 100, about 150, about 200 or about 220 mEq/L.

As used herein, the term "low urinary sodium" generally refers to less than about 20 mEq/L in a urine sample when measured in a one-time urine sample with variations occurring due to reporting from different laboratories. Typically, a normal urine sodium value is about 20 mEq/L and can generally range from about 40 to about 220 mEq/L per day (or about 40 to about 220 mmol per day) for a urine sample collected over a 24-hour time period depending on the dietary salt intake. Other examples of low urinary sodium values range are generally less than about 40 mEq/L. In general, urine samples are normally collected over a 24-hour time period.

As used herein, the term "urinary potassium" refers to the presence of potassium ion in a volume of urine. In general, urinary potassium excretion is regulated by serum potassium concentration and may be assessed via a 24-hour urine potassium collection. In one example, a urinary potassium excretion of an individual with hypokalemia is lowered to less than about 25 mEq/day based on a 24-hour collection. In another example, urinary potassium excretion to less than about 15 mEq/L based on a 24-hour collection may indicate hypokalemic status in an individual. In another example, urine potassium concentration exceeding 40 m Eq/L may also be observed in an individual with hypokalemia. In another example, potassium to creatinine ratio of less than about 1.5 mEq potassium/mmol creatinine may be observed in an individual with hypokalemia. In another example, a potassium-to-creatinine ratio greater than about 20 mEq/g creatinine has been suggested to indicate the presence of hypokalemia in an individual. Furthermore, one method of practicing the present invention of testing for urinary potassium excretion is to measure spot urine potassium in a morning sample due in part to diurnal variations.

As used herein, the term "urinary pH" generally refers to a measure of how acidic or alkaline (basic) a volume of urine is.

As used herein, the term "creatine" generally refers to a breakdown product of creatine phosphate derived from muscle and protein metabolism. Creatinine can be removed from the blood chiefly by the kidneys and is released at a constant rate by the body depending in part on the muscle mass of an individual. In one example, urine values for creatinine range from about 955 to 2,936 milligrams (mg) per 24-hour time frame for males; and about 601 to about 1,689 mg per 24-hour time frame for females, depending on age and amount of lean body mass of the individual with variations occurring due to reporting from different laboratories. In another example, urine values for creatinine based on a 24-hour time frame for urine collection range from about 500 to about 2000 mg/day (or about 4,420 to about 17,680 mmol/day) depending on age and amount of lean body mass. In a third example, urine values for creatine range from about 14 to about 26 mg per kg of body mass per day for men (or about 123.8 to about 229.8 μmol/kg/day) and about 11 to about 20 mg per kg of body mass per day for women (or about 97.2 to about 176.8 μmol/kg/day). In a fourth example, urine values for creatinine for males range from about 0.8 to about 1.8 g/day (or about 7 to about 16 mmol/day), and urine values for females range from about 0.6 to about 1.6 g/day (or about 5.3 to about 14 mmol/day). In a fifth example, urine creatinine concentrations range from about 40 to about 300 mg/dl in males; and about 37 to about 250 mg/dl in females.

As used herein, the term 'specific gravity" of urine generally refers to ratio of the density of urine to a density of a standard substance, such as water. Furthermore, the specific gravity of urine refers to a ratio of the density of urine to the density of water at the same temperature and pressure. In addition, the term "specific gravity is meant to encompass the ratio of the mass of a solution compared to the mass of an equal volume of water when practicing the present invention. Typically, the normal specific gravity of urine ranges from about 1.005 to about 1.030 with variations occurring due to reporting from different laboratories. The terms "urine specific gravity" and "specific gravity of urine" are used interchangeably herein.

As used herein, the term "clean sample" or "clean catch sample" generally refers to a sample of urine that is substantially free of blood, dirt, particulate, microparticulate, one or more COVID-19 antigens, one or more COVID-19 antibodies, COVID-19 RNA material, feces, or the like. Furthermore, the term "clean sample" or "clean catch sample" is meant to encompass a urine sample in which germs from the penis or vagina are prevented from being present. In one example, a clean sample of urine is obtained by filtering the urine sample through a microfiltration membrane. In another example, a clean sample of urine is obtained by filtering a urine sample through an ultrafiltration membrane. In another example, a clean sample of urine is obtained by filtering a urine sample through a nanofiltration membrane. In another example, a clean sample of urine is obtained by removing suspended solids, bacteria, virus, blood, feces from a urine sample.

As used herein, the term "urine bicarbonate" or "bicarbonate in urine" generally refer to the concentration or level of bicarbonate in urine and is reported in millimolar for a specific pH.

As used herein, the term "urine osmolality" is used to measure the number of dissolved particles per unit of water in the urine. In general, normal urine osmolality after a 12 to 14-hour fluid restriction is typically more than about 850 milliOsmality (mOsm)/kg water (SI units). In another example, a random urine specimen has an osmolality of about 50 to about 1200 mOsm/kg water, depending on fluid intake (or about 50 to about 1200 mmol/kg water (SI units)). In a third example, an individual with a normal diet and normal fluid intake has a urine osmolality of approximately 500 to 850 mOsm/kg water. In a fourth example, an osmolality of about 40 to about 80 mOsm/kg water has been observed as a minimal urine osmolality.

The present invention generally includes detecting, measuring and/or monitoring one or more ions, one or more minerals, or any combination thereof in a volume of urine to indicate the presence of a COVID-19 infection or illness. More specifically, the present invention includes detecting, measuring and/or monitoring changes over a specified timeframe in the levels of one or more ions, one or more minerals, or any combination thereof, in a volume of urine. Exemplary ions or minerals of the present invention include one or more hydrogen, hydroxyl, sodium, potassium, chloride, calcium, magnesium ions, or combination thereof. The present invention further includes measuring and/or monitoring body temperature levels and/or blood pressure values in an individual in combination with detecting, measuring, and/or monitoring changes to urinary ionic levels or concentrations to indicate the presence or absence of a COVID-19 infection or illness in an individual. While not wanting to be bound to theory, it is to be understood that detecting, measuring, and/or monitoring of urine samples of the present invention do not require the presence of any COVID-19 antigen, COVID-19 antibody, or COVID-19 RNA material to indicate the presence of a COVID-19 infection or illness.

In general, detection, measurement, and/or monitoring mineral and/or ionic concentrations or levels are typically performed over a specified timeframe when practicing the present invention. In an example, mineral and/or ionic levels are measured every 30 minutes. In another example, pH, urine mineral and/or ionic levels are measured every hour. In another example, urine pH, mineral and/or ionic concentrations are analyzed every 24-hours. In another example, random or spot measurement of urinary pH, mineral and/or ionic levels is performed daily for a period of two weeks to about 30 days. In another example, urinary pH, minerals and/or ionic content is measured every two to three days.

Renin converts angiotensinogen to angiotensin I ("ANG I). Angiotensin-converting enzyme-1, hereinafter referred to as "ACE1" is an important component of the renin-angiotensin system, hereinafter referred to as the "RAS" that cleaves or converts ANG I into angiotensin II ("ANG II"). ANG II is responsible for inflammation and high blood pressure. ANG II attaches or binds to angiotensin II type 1 receptor and works to induce vasoconstriction, aldosterone secretion stimulation, hypokalemia, and pulmonary epithelium degradation. Angiotensin-converting enzyme-2, hereinafter referred to as "ACE2" is also an important component of RAS that is generally found on the surfaces of the lung, intestine, heart, GI tract and liver. ACE2 is used to lower blood pressure by catalytically converting ANG II into a series of metabolites or into ANG 1-7 metabolites. By converting ANG II into ANG 1-7, ACE2 reduces ANG II levels as well as decreases the effect of ANG II since ANG II is degraded into ANG 1-7 metabolites that function as vasodilators, which are known to modulate blood pressure. Therefore, RAS and/or the renin-angiotensin-aldosterone system (hereinafter referred to as "RAAS") regulates blood pressure, plasma potassium, fluid and electrolyte balance, and systemic vascular resistance in humans through ANG I and ANG II.

As noted above, SARS-CoV-2 is the virus that causes COVID-19 infection or illness. ACE2 has been implicated in the etiology of SARS-CoV-2. While not wanting to be bound to theory, it is believed that "SARS-CoV-2 virus" or "SARS-CoV-2" (used interchangeably herein) uses a receptor of ACE2 to penetrate a human host cell during the infection phase of SARS-CoV-2. SARS-CoV-2 binding to ACE2 receptors leads to downregulation of ACE2 and/or an overall increase in ANG II. With the decrease in ACE2 activity, less ANG II conversion to ANG 1-7 metabolites were observed which may result in greater cellular injury by ANG II. This might be why ACE2 receptors are believed to function as a COVID-19 "virus hook" or "cellular doorway" for the COVID-19 virus during infection in humans. Furthermore, as harmful ANG II effects are typically reduced by ACE2 activity, COVID-19 virus binding to ACE2 receptors prevent ACE2 binding and/or normal operation which may result in more ANG II-mediated cellular injury.

ANG II typically increases aldosterone secretion, which is also known to mediate calcium, sodium, potassium, and other ionic levels in cells, and to modulate blood pressure. Therefore, it is believed SARS-CoV-2 may impair regulation of RAAS. As such, COVID-19 virus binding to ACE2 receptor to enter and infect human cells may be considered a form of RAAS dysregulation.

In healthy individuals, nearly all potassium filtered by the kidneys are reabsorbed to maintain optimal potassium levels. Typically, potassium excretion is stimulated by aldosterone and/or in response to dietary intake of potassium to modulate optimal potassium levels. Higher prevalence of hypokalemia have been shown among severely ill patients with COVID-19. In one example, clinical data among patients with COVID-19 show a high proportion classified as having severe hypokalemia (blood plasma potassium of less than about 3 mmol/L) and hypokalemia (blood plasma potassium levels of about 3 to about 3.5 mmol/L).

It has been discovered that the onset of hypokalemia observed during a COVID-19 infection may be detected by measuring and/or monitoring potassium ion levels in urine in an individual, such as over a 1-day, or a 3-day period of time, or a 5-day period of time, or a 7-day period of time, or a 10-day period of time, or a 14-day period of time, or a 21-day period of time, a 31-day period of time or before, during and after a COVID-19 infection. Hypokalemia in an individual may be detected, measured, and/or monitored by observing urinary potassium levels of greater than normal urinary potassium levels, such as more than 15 mEq/L (typically measured over a 24-hour timeframe). While not wanting to be bound to theory, it is believed that hypokalemia in an individual results in the release of potassium into the urine. Typically, normal or reference values for urinary potassium levels ranges from about 25 to about 125 mEq/24-hr collection timeframe using a urine sample. A sudden increase in daily urinary potassium levels, such as an increase of about 10%, about 15%, about 20%, about 30%, about 40%, or about 50% when compared to one or more prior measured, monitored, and/or detected urinary potassium levels may indicate the onset of a COVID-19 infection. Similarly, urinary potassium levels or concentrations of more than about 50 mEq, more than about 75 mEq, more than about 80 mEq, more than about 85 mEq, more than about 90 mEq, more than about 95 mEq, or more than about 125 mEq over a 24-hour collection may suggest COVID-19 virus binding. In an example, a spot urine potassium sample having more than about 100 mEq/L to about 125 mEq/L may suggest a COVID-19 infection.

In general, daily monitoring of urinary potassium levels will establish normal urinary potassium levels prior to the onset of a COVID-19 infection. While not wanting to be bound to theory, it is believed changes from normal urinary potassium to higher urinary potassium levels due to blood potassium losses at the start of an COVID-19 infection may be effective to indicate the start of a COVID-19 infection. Thus, an increase in urinary potassium levels (or urine samples containing high levels of potassium) when compared to prior measured, monitored and/or detected urinary potassium values may correlate to the onset of a COVID-19 infection.

Furthermore, while not wanting to be bound to theory, it is believed urinary potassium levels remain elevated for a period of time due to RAS dysregulation and/or hypokalemia during a COVID-19 infection. This time period may vary due to the severity of a COVID-19 infection or illness. In one example, urinary potassium levels remain about 10% higher, about 20% higher, about 30% higher or about 50% higher than previously measured, monitored and/or detected urinary potassium levels for at least 72 hours. In another example, urinary potassium levels remain higher than about 125 mEq per L for at least about 48 hours due to the onset or ongoing COVID infection. In a third example, urinary potassium levels remain higher than about 50, about 75, about 100 mEq/L for at least about five days due to a COVID infection. Furthermore, once the COVID-19 infection passes and the body normalizes (recovers or heals), it is believed urinary potassium levels drop to normal levels of about 25 to about 125 mEq/day (or other normal urinary potassium range for an individual) once hypokalemia is resolved and/or the COVID-19 infection goes away. Therefore, daily measurement of urinary potassium levels, in a fasted state for example, to detect abnormal increases in urinary potassium is believed effective to detect the onset, duration and completion of a COVID-19 infection in healthy, symptomatic and/or asymptomatic individuals.

Sodium may also be filtered by the kidneys to maintain optimal sodium levels in healthy individuals. It has been discovered that the onset of a COVID-19 infection may also be detected by measuring and/o monitoring urinary sodium levels in an individual over an extended period of time, such as over a 1-day, or a 3-day period of time, or a 5-day period of time, or a 7-day period of time, or a 10-day period of time, or a 14-day period of time, or a 21-day period of time, a 31-day period of time or before, during and after a COVID-19 infection.

Urinary sodium levels fluctuate within a normal range of about 40 to about 220 mEq/L prior to infection by COVID-19. While not wanting to be bound to theory, it is believed that the onset of a COVID-19 infection may result in a decrease in urinary sodium levels. A sudden decrease in daily urinary sodium levels, such as by more than about 5%, more than about 10%, more than about 20%, or more than about 35% may indicate sodium retention or an elevation in blood sodium levels.

As such, it is believed a sudden decrease in daily urinary sodium levels, such as a decrease of about 10%, about 15%, about 20%, about 30%, about 40%, or about 50% when compared to one or more prior measured, monitored and/or detected urinary sodium levels may indicate the onset of a COVID-19 infection. Similarly, urinary sodium levels or concentrations of less than about 40, less than about 30, less than about 25, less than about 20, or less than about 15 mEq/L over about a 24-hour timeframe may suggest COVID-19 virus binding to ACE2 receptors. In an example, a urine sodium test sample having less than about 20 mEq/L may suggest a COVID-19 infection. In another example, less than about 40, less than about 30, less than about 25, less than about 20, or less than about 15 mmol urinary sodium per day based on a 24-hour urine collection may suggest the onset of a COVID-19 infection.

In general, daily monitoring or urinary sodium levels may help to establish normal urinary sodium levels prior to the onset of a COVID-19 infection or illness. While not wanting to be bound to theory, it is believed changes from normal urinary sodium to lower urinary sodium levels occurs at the start of an COVID-19 infection and this change may be effective to indicate the start of a COVID-19 infection or illness. Thus, an increase in urinary sodium levels (or urine samples containing high levels of sodium) when compared to prior measured, monitored and/or detected urinary sodium values may correlate to the onset of a COVID-19 infection.

Furthermore, while not wanting to be bound to theory, it is believed urinary sodium levels remain lower than normal urinary sodium levels for a period of time during a COVID-19 infection or illness. This time period may vary due to the severity of a COVID-19 infection or illness. In one example, urinary sodium levels remain about 10% lower, about 20% lower, about 30% lower or about 50% lower than previously measured, monitored and/or reported urinary sodium levels for at least 72 hours. In another example, urinary sodium levels remain lower than about 40 mEq per L for at least two days or 48 hours due to the onset or ongoing COVID infection. In a third example, urinary sodium levels remain lower than about 200, about 150, about 100 mEq/L for at least five days due to a COVID infection.

Furthermore, once the infection passes, the body normalizes (recovers or heals) urinary sodium levels increase to normal levels of about 40 to about 220 mmol per day (or other normal urinary sodium ranges for the individual) based on a 24-hour collection timeframe. Therefore, daily measurement of urinary sodium levels, in a fasted state for example, to detect abnormal decreases in urinary sodium is believed effective to detect the onset, duration and completion of a COVID-19 infection in healthy, symptomatic and/or asymptomatic individuals.

A COVID-19 infection may also result in an elevated or higher body temperature than the normal body temperature of about 97° F. (36.1° C.) to about 99° F. (37.2° C.) in some individuals. As such, periodic and/or daily monitoring of body temperature is also believed effective to detect the onset, duration and/or completion of a COVID-19 infection along with detection, measuring, and/or monitoring one or more ions, one or more minerals, or any combination thereof when practicing the present invention. In one example, an individual body temperature of more than about 100.4° F. (38° C.) along with urinary potassium levels of more than about 20 mEq/L may indicate a COVID-19 infection has started based on prior measured, monitored and/or detected normal body temperatures and urinary potassium levels.

A COVID-19 infection may also result in an elevated or higher blood pressure than the normal blood pressure in some individuals. As such, periodic and/or daily monitoring of body pressure is believed effective to detect the onset, duration and/or completion of a COVID-19 infection along with detection, measuring, and/or monitoring one or more ions, one or more minerals, or any combination thereof when practicing the present invention. In one example, an individual blood pressure greater than the normal blood pressure of an individual, such as more than about 110 mm Hg to about 144 mm Hg (systolic), about 70 mm Hg to about 81 mm Hg (diastolic), and urinary sodium level of less than about 20 mEq/L indicates a COVID-19 infection has started based on a prior measurement, such as about a prior 24-hour measurement of normal blood pressure and urinary sodium levels.

Calcium is one of the most abundant minerals in the human body. The body normally keeps serum and intracellular calcium levels under tight control through bone resorption and urinary excretion. Furthermore, reference ranges of urinary calcium are dependent on the diet, intestinal absorption, with variations often reported amongst different laboratories.

It has been discovered that the onset of a COVID-19 infection may also be detected by measuring urinary calcium levels in an individual over an extended period of time, such as over about a 3-day period of time, or about a 5-day period of time, or about a 7-day period of time, or about a 10-day period of time, or about a 14-day period of time, or about a 21-day period of time, about a 31-day period of time, or before, during and after a COVID-19 infection.

Typically, urinary calcium levels fluctuate within a normal range of about 100 mg/day to about 250 mg/day based on a 24-hour collection time frame prior to infection by COVID-19. In one example, urinary calcium levels range from about 15 mmol to about 20 mmol per day, based upon a 24-hour collection timeframe.

While not wanting to be bound to theory, it is believed that upon COVID-19 infection, urinary calcium levels drop significantly, such as more than about 5%, more than about 10%, more than about 20%, or more than about 35% as reflected by calcium retention or an elevation in blood calcium, blood serum calcium, and/or serum ionized calcium levels. A decrease in daily urinary calcium levels, such as a decrease of about 10%, about 15%, about 20%, about 30%, about 40%, or about 50% when compared to one or more prior measured, monitored and/or reported urinary calcium levels may indicate an onset of a COVID-19 infection. Similarly, urinary calcium levels or concentrations of less than about 50, less than about 40, less than about 30, less than about 20, or less than about 15 mg over a 24-hour timeframe may suggest a COVID-19 infection. In an example, a urine calcium sample having about 50 to about 150 mg calcium per 24-hour timeframe may be due to a COVID-19 infection. In another example, less than about 150, less than about 120, less than about 100, less than about 80, or less than about 60 mg calcium per day based on a 24-hour collection may suggest the onset of a COVID-19 infection.

In general, daily monitoring of urinary calcium will establish normal urinary calcium levels prior to the onset of a COVID-19 infection. While not wanting to be bound to theory, it is believed changes from normal urinary calcium levels to a decrease in urinary calcium levels (or urine samples containing lower levels of calcium) when compared to prior measured, monitored and/or detected urinary calcium values may correlate to the onset of a COVID-19 infection.

Furthermore, while not wanting to be bound to theory, it is believed that urinary calcium levels remain decreased during a COVID-19 infection for a period of time. The time period may vary due to the severity of the COVID-19 infection. In one example, urinary calcium levels remain lower for at least about one day. In another example, urinary calcium levels remain about 10% lower, about 20% lower, about 30% lower or about 50% lower than previously measured, monitored and/or detected urinary calcium levels for about 72 hours during a COVID infection or illness resulting from the COVID-19 infection. In another example, urinary calcium levels remain lower than about 150 mg per day for at least about 48 hours due to a COVID infection or illness derived from a COVID19 infection. In a third example, urinary calcium levels remain lower than about 20 mg per day for at least about five days due to a COVID-19 infection or illness.

Furthermore, once a COVID-19 infection or illness passes, it is believed calcium levels normalize (recovers or heals), and blood serum calcium or serum ionized calcium levels return to normal levels for an individual. The effect is an increase in urinary calcium levels to normal levels of about 20 to about 250 mg per day for women, about 20 to about 300 mg per day for men, or whatever calcium ranges are considered normal for the individual, based on a 24-hour urine collection. Daily measurement of urinary calcium levels, in a fasted state for example, to detect abnormal decreases in urinary calcium is believed effective to detect the onset, duration and completion of a COVID-19 infection in healthy, symptomatic and/or asymptomatic COVID individuals.

A COVID-19 infection may also result in observing an elevated or higher blood pressure than ranges believed normal for an uninfected individual along with observation in fluctuations in urinary calcium levels. As such, periodic and/or daily monitoring of body pressure is believed effective to detect the onset, duration and/or completion of a COVID-19 infection when performed in combination with detection, measurement and/or quantification of one or more urinary ions, one or more urinary minerals, or any combination thereof when practicing the present invention. In one example, an individual's blood pressure that is greater than the normal blood pressure range for the individual, such as more than about 110 mm Hg to about 144 mm Hg (systolic) and about 70 mm Hg to about 81 mm Hg (diastolic), along with urinary calcium levels of less than about 20 mg per day may indicate a COVID-19 infection has started when compared to prior monitored, detected and/or measured blood pressure and urinary calcium measurements.

It has been discovered that the onset of a COVID-19 infection may also be detected by measuring, quantifying and/or monitoring urinary chloride ion levels in an individual. While not wanting to be bound to theory, it is believed that a COVID infection in an individual results in release of chloride into the urine. Typically, normal or reference values for urinary chloride levels ranges from about 110 to about 250 mEq per Liter per day based on a 24-hour collection timeframe although higher or lower reference values have been reported based on the amount of water ingested, laboratory protocol, or the like. In one example, normal urinary chloride ranges from about 140 to about 250 mEq per Liter per 24-hour timeframe.

A sudden increase in daily urinary chloride levels, such as an increase of about 10%, about 15%, about 20%, about 30%, about 40%, or about 50% when compared to one or more prior urinary chloride levels may indicate the onset of a COVID-19 infection. Similarly, urinary chloride levels or concentrations of more than about 40, more than about 50, more than about 75, more than about 100, more than about 125, or more than about 200 mEq per liter per 24-hour collection may suggest a COVID-19 infection. For example, a urine chloride sample having more than about 40 mmol per Liter may suggest a COVID-19 infection.

In general, daily monitoring of urinary chloride levels will establish baseline and/or normal urinary chloride levels prior to the onset of a COVID-19 infection. While not wanting to be bound to theory, it is believed changes from normal urinary chloride to higher or increased urinary chloride levels (or urine samples containing high levels of chloride) when compared to prior monitored, measured, detected, or recorded urinary chloride values may correlate to the onset of a COVID-19 infection.

Furthermore, it is believed urinary chloride levels remain elevated for a period of time during a COVID-19 infection. The time period may vary due to the severity the COVID-19 infection or illness. In one example, urinary chloride levels remain about 10% higher, about 20% higher, about 30% higher or about 50% higher than previously reported, monitored, and/or measured urinary chloride levels for at least about 24 hours. In another example, urinary chloride levels remain higher than about 100 mEq per L per 24 hours for at least about 48 hours due to a COVID infection or illness. In a third example, urinary chloride levels remain higher than about 50, about 75, about 100 mmol per Liter for about five days due to a COVID infection or illness.

It is also believed that once the COVID-19 infection passes and the body normalizes (recovers or heals), urinary chloride levels return to normal levels of about 110 to about 250 mEq per liter per 24 hours (or to the ranges are considered normal for the individual). Therefore, daily measurement of urinary chloride levels, in a fasted state for example, to detect abnormal increases in urinary chloride is believed effective to detect the onset, duration and/or completion of a COVID-19 infection (or illness) in healthy, symptomatic and/or asymptomatic individuals.

As noted above, a COVID-19 infection may result in an elevated or higher body temperature than the body temperature of an uninfected individual. As such, periodic and/or daily monitoring of body temperature is believed effective to detect the onset, duration and/or completion of a COVID-19 infection when performed along with detecting, measuring, monitoring urinary chloride ion measurements in the present invention. In one example, an individual body temperature of more than about 99° F. along with a urinary chloride level of more than about 40 mEq/L may indicate a COVID-19 infection has started when compared to prior normal body temperatures and urinary chloride levels.

It has been discovered that the onset of a COVID-19 infection may also be detected by monitoring urinary magnesium ion levels in an individual. While not wanting to be bound to theory, it is believed that a COVID infection in an individual results in release of magnesium into the urine. Typically, normal or reference values for urinary magnesium levels ranges from about 51 to about 269 mg per 24-hour day based on a 24-hour collection timeframe. A sudden increase in daily urinary magnesium levels, such as an increase of about 10%, about 15%, about 20%, about 30%, about 40%, or about 50% when compared to one or more prior detected, monitored or measured urinary magnesium levels may indicate the onset of a COVID-19 infection. Similarly, urinary magnesium levels or concentrations of more than about 24, more than about 50, more than about 75, more than about 100, more than about 125, or more than about 200 mg per 24-hour collection may suggest a COVID-19 infection or illness.

In general, daily monitoring of urinary magnesium levels may help to establish normal urinary magnesium levels prior to the onset of a COVID-19 infection. While not wanting to be bound to theory, it is believed changes from normal urinary magnesium levels to higher urinary magnesium levels (or urine samples containing high levels of magnesium) when compared to prior recorded, monitored, detected or measured urinary magnesium values may correlate to the onset of a COVID-19 infection.

Furthermore, it is believed urinary magnesium levels remain elevated for a time period during a COVID-19 infection. This time period may vary due to the severity of a COVID-19 infection or illness. In one example, urinary magnesium levels remain about 10% higher, about 20% higher, about 30% higher or about 50% higher than previously recorded, measured, or monitored urinary magnesium levels for at least about 12 hours. In another example, urinary magnesium levels remain higher than about 100 mg per 24 hours for at least about 48 hours due to a COVID infection or illness. In a third example, urinary magnesium levels remain higher than about 150, about 175, or about 200 mg per 24-hours for at least about 72 hours due to a COVID infection or illness.

It is also believed that once the COVID-19 infection passes and the body normalizes (recovers or heals), urinary magnesium levels return to normal levels of about 51 to about 269 per 24 hours (or to ranges that are considered normal or baseline for the uninfected individual). Therefore, daily measurement of urinary magnesium levels, in a fasted state for example, may be used to detect abnormal increases in urinary magnesium and is believed effective to detect the onset, duration and completion of a COVID-19 infection in healthy, symptomatic and/or asymptomatic individuals.

The urinary pH for an individual typically ranges from about 4.5 to about 8.0 in the absence of a COVID-19 infection or illness. In one example, the urinary pH of an adult is slightly acidic and ranges from about 6.0 to about 7.5. The urinary pH of an individual designated as having a COVID-19 infection or illness generally decreases and becomes more acidic. In an example, the urinary pH of an individual infected with COVID-19 ranges from about 7.5 to about 7.0, to about 6.5, to about 6.4, to about 6.3, to about 6.2, to about 6.15, to about 6.10, to less than about 5.99 during the duration of the COVID-19 infection and/or illness.

In general, daily monitoring of urinary pH levels will help establish normal or baseline urinary pH (about 4.5 to about 8.0) values prior to the onset of a COVID-19 infection when practicing the present invention. While not wanting to be bound to theory, it is believed changes from normal or baseline urinary pH values to an increase in urinary acidity or reduction in urinary pH may be effective to indicate the start of a COVID-19 infection when compared to prior measured, monitored, quantified urinary pH values.

It is believed urinary pH levels remain acidic during a COVID-19 infection for a period of time. The time period may also vary due to the severity of a COVID-19 infection or illness. In one example, urinary pH levels remain about 10% lower, about 20% lower, or about 30% lower than previously detected, recorded, monitored, measured, and/or reported urinary pH levels for at least about 12 hours. In another example, urinary pH levels remain lower than a pH of about 7.0 for at least about 24 hours due to a COVID infection or illness. In a third example, urinary pH levels remain lower than normal or baseline urinary pH values for about 48 hours due to a COVID infection or illness.

Furthermore, once the COVID-19 infection or illness passes and the body normalizes (recovers or heals), urinary pH levels are expected to return to normal or baseline levels of about 6.5 to about 8.0 (or to the normal or baseline range of urinary pH values for the individual prior to an infection). Therefore, daily measurement of urinary pH levels, in a fasted state for example, may be used to detect abnormal increases in urinary pH and is believed effective to detect the onset, duration and completion of a COVID-19 infection in healthy, symptomatic and/or asymptomatic individuals.

In general, any suitable thermometer that is effective to measure the body temperature of an individual may be used to detect, measure, monitor and/or record the body temperature of an individual when practicing the present invention. No-touch forehead, body thermometers, and/or other temperature measuring devices are considered suitable for use when practicing the present invention. For example, a suitable device is IHEALTH® No-Touch Forehead Thermometer, Digital Infrared Thermometer for Adults and Kids, Touchless Baby Thermometer with 3 Ultra-Sensitive Sensors, Large LED Display and Gentle Vibration Alert (PT3). Alternatively, one could use a smart phone equipped with a good thermometer app to monitor, measure, record daily body temperatures when practicing the present invention.

In general, any suitable blood pressure device can be used when practicing the present invention. An example is the 10 Series® Wireless Upper Arm Blood Pressure Monitor. Alternatively, a smart watch adapted to measure and record the blood pressure on an individual may also be used when practicing the present invention.

Urinary ions and/or minerals of the present invention, such as sodium, hydrogen, hydroxyl, potassium, calcium, chloride, magnesium, bicarbonate, or the like may be detected, measured, monitored and/or recorded using one or more ion test kit(s), one or more ion test strip(s), one or more ion probe(s), one or more ion testing devices, one or more urine analyzer(s), or any combination of any of these.

The test device 100 of the present invention generally includes housing 102 that encloses a urine reception area 104 and a urine analyzing area 106 as depicted in FIG. 1. The housing encloses one or more detecting components 200 configured to detect and/or measure one or more ion(s) and/or one or more minerals present in urine. The housing 102 further includes an analyzing component 300 that analyzes the detected or measured ions(s) or minerals in the urine sample and a display component 400 for viewing one or more assay results. The housing 102 may optionally contain a memory component 500.

Figure 2:
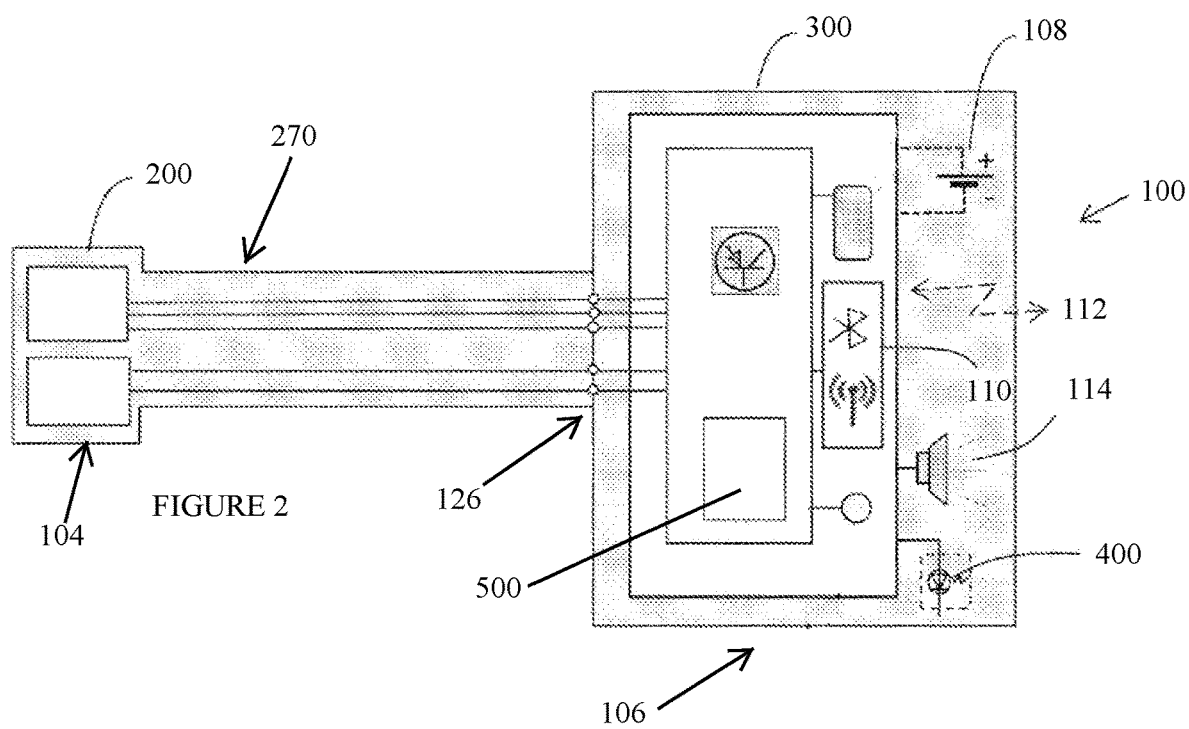
FIG. 2 is a block diagram of the testing device in accordance with a second embodiment of the present invention.

The housing 102 also includes a power component 108, such as a small button cell or battery, to deliver electrical power to the test device, and, optionally, a wireless component 110 in electronic communication with a wireless link 112 for transmission and/or receipt of data or information. A sound emitting component 114, including for example a beeper or buzzer, may also be included, as depicted in FIG. 2. The housing 102 of the test device generally employs a two-part construction with a top part 116a and a bottom part 116b of identical construction as depicted in FIG. 1. The housing 102 may be generally formed of synthetic plastic material, such as polycarbonate or polypropylene, and may optionally include an opacifier to render the plastic material opaque. However, one skilled in the art will recognize that the housing 102 may be constructed of other suitable materials without departing from the spirit of the present invention.

Figure 3:
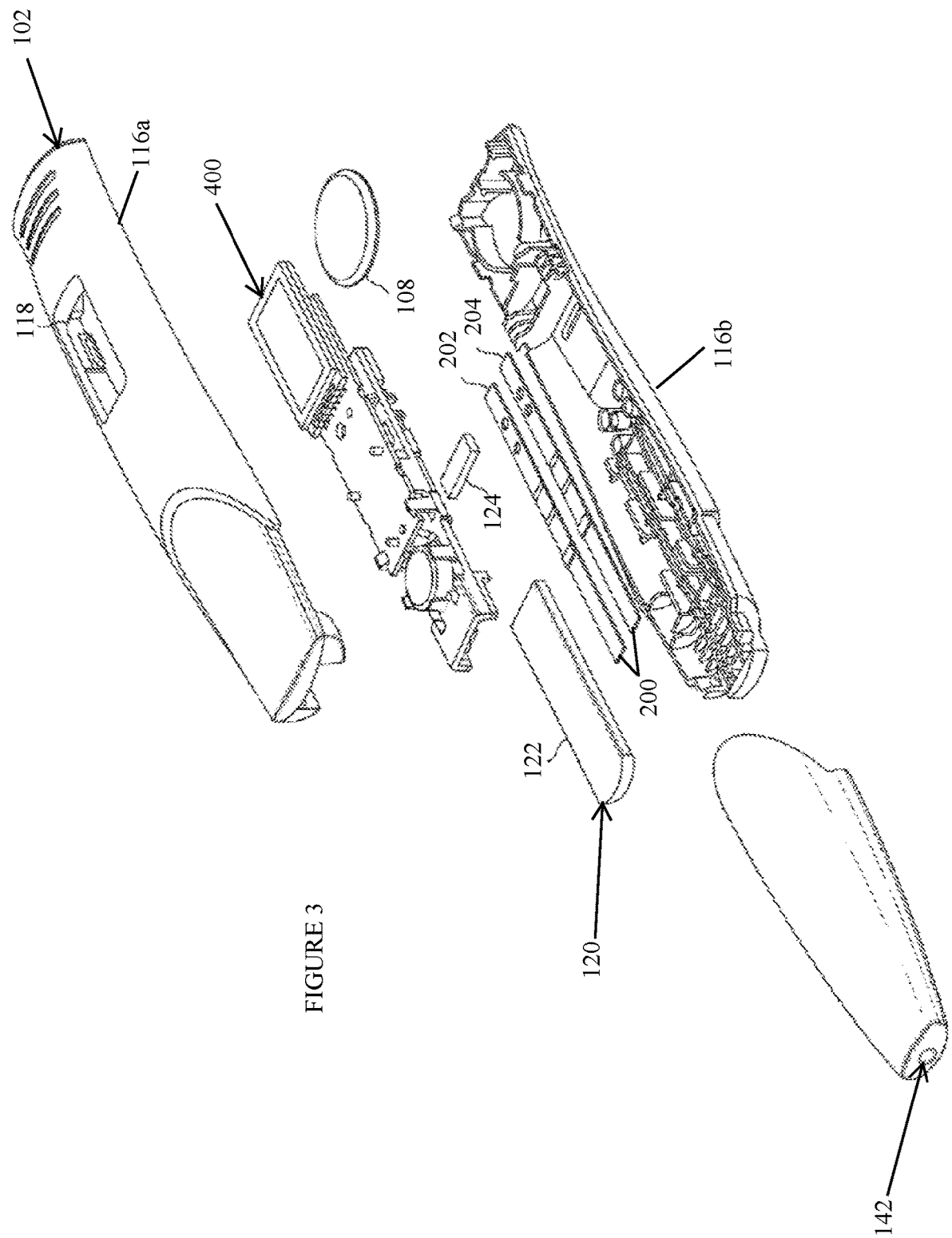
FIG. 3 is a right-side exploded view of the testing device in accordance with a third embodiment of the present invention.

In one example, housing 102 may also include a viewing window 118 as part of the display component 400 on both halves of the housing 102 through which the results of the ion test assays can be viewed after measurement or detection. The viewing window 118 typically defines a central channel that receives one or more test strips, displays one or more assay results in the form of color changes, indicator bands, or one or more LED lights that emit light based on assay results, as depicted in FIG. 3. In addition, the urine reception area 104 includes a sample application zone 120 located on a sample application member 122 that extends from housing 102 to allow a urine sample to be applied or placed in contact with the testing device, as is known in the art. The urine reception area 104 may be detachably connected to the urine analyzing area 106 through junction 126 in a manner that allows for cleaning or replacement of the urine reception area 104, as depicted in FIGS. 2 and 3.

The test device 100 may contain a chamber that includes a semipermeable component that is effective to retain (or prevent the passage of) bacteria, virus, parasites, microorganisms, suspended particles, or one more colloids, particles, or suspended material from a urine sample while allowing the passage or transport of a filtered urine sample or concentrate containing ions and/or minerals (not shown). Some non-exhaustive examples of suitable semipermeable membranes useful in practicing the present invention include microfiltration membrane, ultrafiltration membranes, nanofiltration membranes, ion permeable membranes, membranes or materials that are effective to remove COVID-19 viral material, antigens and/or antibodies or any combination thereof. The semipermeable membrane is typically effective to produce a clean catch or clean sample for urine analysis. By clean is meant substantially free of dirt, feces, blood particulates, or the like.

The chamber may also include a receiving portion, a concentrate portion, and a channel in fluid communication with the chamber that is effective to transfer the filtered urine sample to an ionic detection receptacle that can detect one or more ions, one or more minerals, or any combination of any of these. The ion detection receptacle may house any suitable ion detecting material, such as the above-mentioned functionalized nanoparticles, any colorimetric, enzymatic, electrochemical, precipitation, flocculation, or other suitable ion and/or mineral detecting component.

In another example, ionic concentration can be detected using two paper-based elements linked to and in fluid communication with each other. For example, one of the two paper-based elements may be a urine separation unit while the second paper-based element may be a colorimetric detection component. After a urine sample is placed on or in the separation unit, the separation unit is effective to clean the urine sample and produce a clean urine substantially free of COVID-19 antigen, COVID-19 antibodies, dirt, blood, other particulate and/or microparticulates for further testing and analysis. The clean urine sample is transported to the detection unit, which generally includes one or more colorimetric, electrochemical, precipitation, flocculation materials, or suitable ion detecting components that are effective to detect and/or quantify the ionic levels in the urine sample and display one or more diagnostic results or colors for analysis.

When the detecting component 200 is in the form of one or more lateral flow assay strips, a sampling wick 122 is placed in liquid communication with strips 202, 204, as is known in the art and depicted in FIG. 3. A first end region of the sampling wick 122 is in liquid communication with an adjacent end region of assay strips 202, 204, thereby enabling the sampling wick 122 to serve as a sample application zone 120. Liquid movement into and along the assay strips 202, 204 may be facilitated by a sink pad 124 is located at a distal end of the wick 122 and in liquid communication with the assay strips 202, 204.

Figure 5:
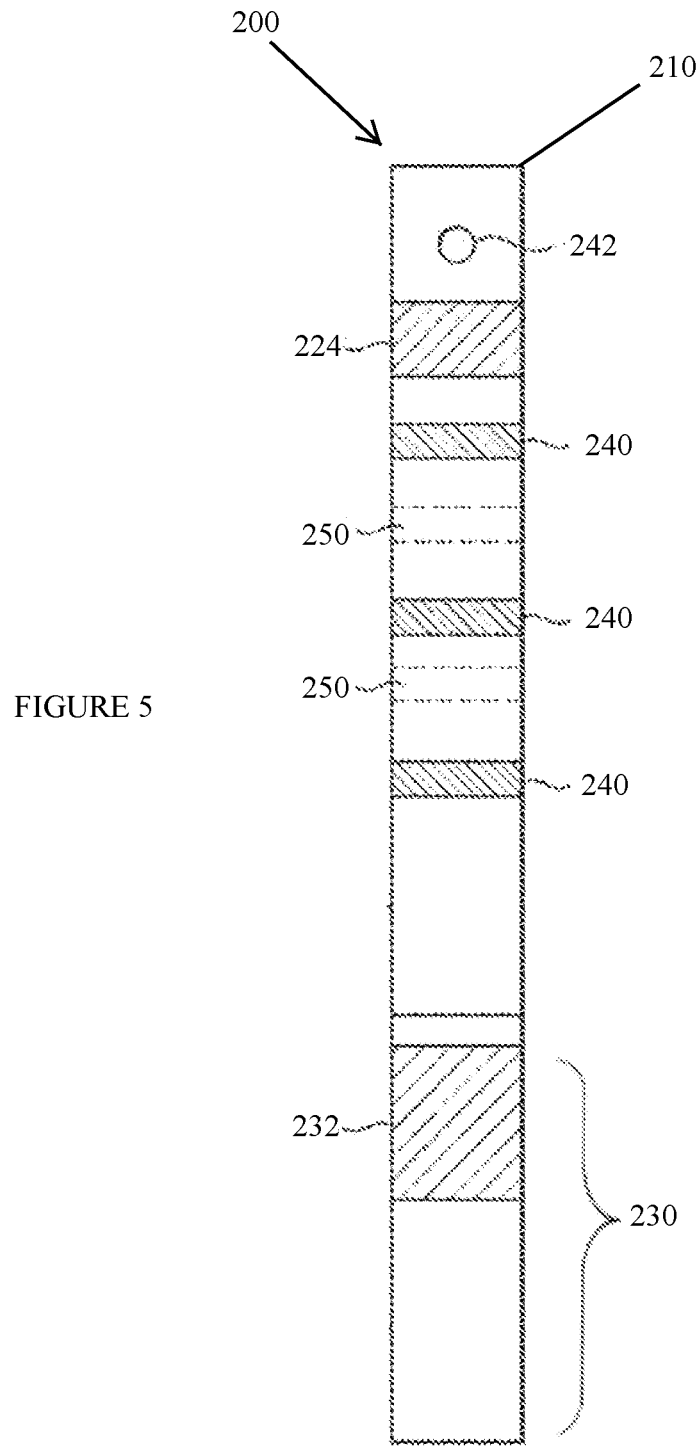
FIG. 5 is a top view of a detecting component in accordance with a first embodiment of the present invention.

In another embodiment, when the detecting component 200 includes two or more assay strips, a common sample application zone in fluid communication with each assay strip can be used even as separate flow paths are maintained for each analyte on the assay strips. An opposing second end region of the sampling wick 122 typically projects through and beyond an aperture 142, opening 142 or port 142 of housing 102 to allow sample to be applied to the sampling wick 122 as is known in the art. The strips 202, 204 may be constructed of nitrocellulose or any other suitable material with a pore size that permits wicking, transport, or movement of an applied liquid along the entire length of the strips 202, 204 via capillary action as depicted in FIG. 5. The sampling wick 122 can also be constructed from absorbent material that helps the urine sample to be absorbed into the wick 122. The urine sample typically flows passively along the wick 122, onto (or into) assay strips 202, 204 in the direction of sink pad 124.

Figure 4:
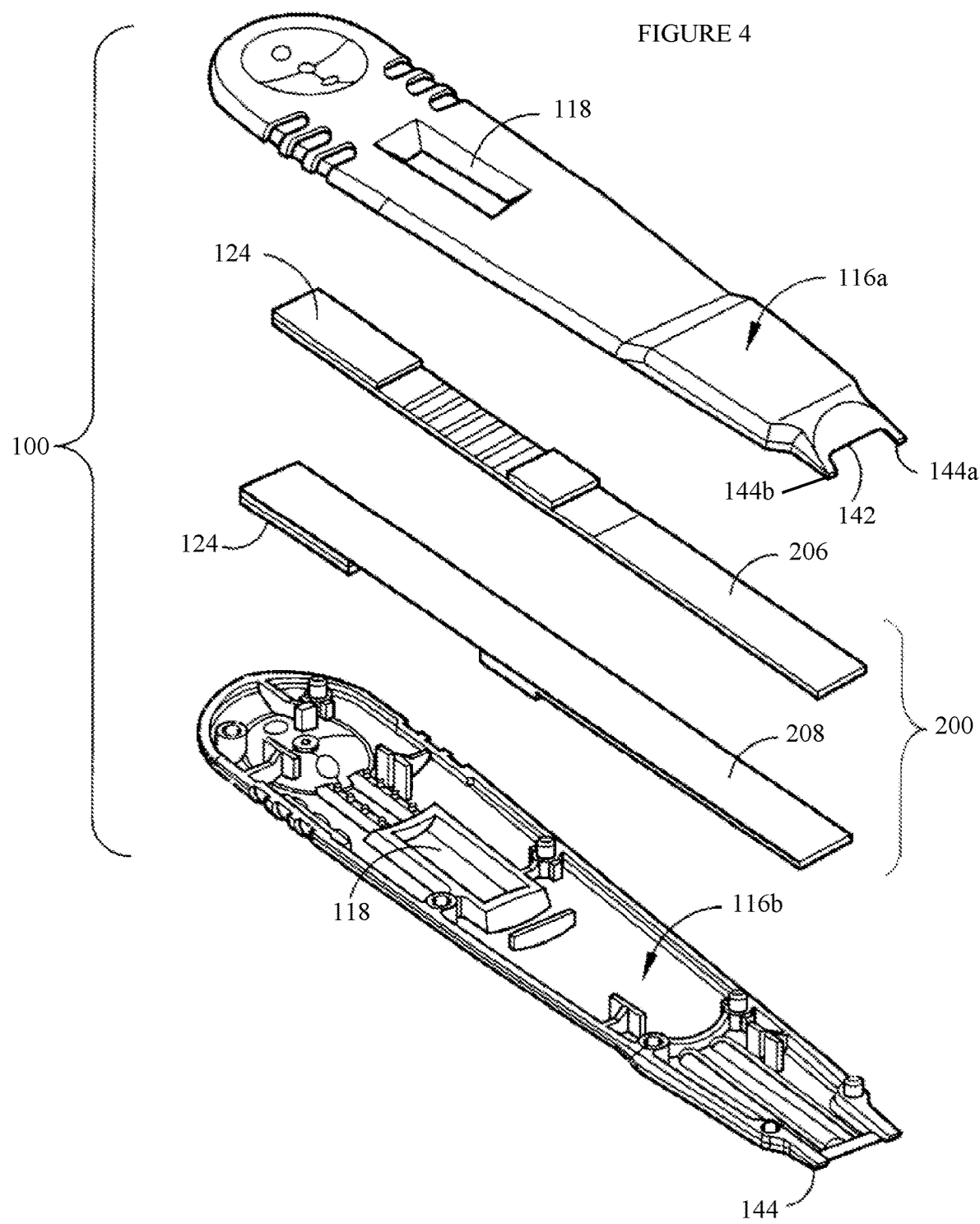
FIG. 4 is a left-side exploded view of the testing device in accordance with a fourth embodiment of the present invention.

In a third embodiment, the detecting component 200 includes two assay strips 206, 208 that are juxtaposed back-to-back with a rear surface further including a sheet of thin backing material, as depicted in FIG. 4. Each detecting component 200 can include a visible label, such as an indicator band, dye composition, color component, or colored latex particles that produce a marking or color change upon detection or measurement. The strips 206, 208 are typically sized so as to extend downward and slightly out of housing halves 116a, 116b through port 142 that allows protrusion or extension into a region between chisel points 144a, 144b. Protrusion of strips 206, 208 allows for contact with and absorption of the urine sample through a common sample application zone in liquid communication with strips 206, 208 during operation of the test device 100.

The detecting component 200 generally includes one or more capture zones 230, one or more detecting zones 240, and/or one or more reference zones 250, as depicted in FIG. 5. The capture zone 230 is generally located at a proximal end of the assay strip 210, which is the end first encountered by a urine sample. Capture zone 230 is in liquid communication with reference zone 240 and/or detection 250 zones. The capture zone 230 can be in the form of a capture pad loaded with one or more reagents capable of binding to one or more analytes in a test sample to facilitate detection.

In the present invention, the capture zone 230 of the test device 100 includes one or more filtering compositions that filter, retain, remove, react with and/or immobilize one or more anions in a urine sample. In one embodiment, the capture zone 230 may be in the form of an ion complexing composition like a polyelectrolyte composition that filters, removes, retains, or prevents the movement of anions, for example hydroxyl and/or chloride ions, in a urine sample. As used herein, the term "polyelectrolyte" refers to macromolecules that, when dissolved in a polar solvent like water, have a number of charged groups covalently linked to them. In addition, the term "polyelectrolyte" is meant to encompass polymers whose repeating units bear an electrolyte group that can dissociate in an aqueous solution, such as water to render the electrolyte group charged. In this embodiment, it is believed filtering, removing, retaining or preventing the movement of urinary anions, such as hydroxyl and/or chloride ions, helps improve selectivity of urinary cations like urinary potassium and sodium. In another example, the capture zone 230 contains ion permeable membrane materials, such as cation exchange membrane materials. Cation exchange membrane materials include a polymer backbone with functional groups, including for example sulfonic acid residues capable of binding one or more cations while repelling one or more anions. Cation exchange membranes permit the transfer of cations like mono- and divalent cations while minimizing most, if not all, transfer of anions, such as hydroxyl and chloride ions. Use of cation exchange membrane materials are believed to be helpful in enhancing detection and/or measurement of urinary sodium ions in the presence of urinary potassium ions after removal, retention, filtering, hindering, or immobilization of anions in a test sample. As such, preventing the transport or movement of anions in the capture zone while allowing cations to pass through is designed to enhance the ability to distinguish between ions and enhance ion selectivity when other ions may be present in a urine sample. In another embodiment, the capture zone is in the form of a complex that retains cations in combination with an anion selective electrode for removal of cations while permitting anions to be detected in the detection zone.

Alternatively, inclusion of a detection band 232 within the capture zone 230 to detect one or more anions may be included in accordance with the present invention to detect and measure anions in the capture zone 230. In this alternative embodiment, detection and/or measurement of anions prior to cation detection and/or measurement can be helpful to determine COVID-19 status.

Figure 6:
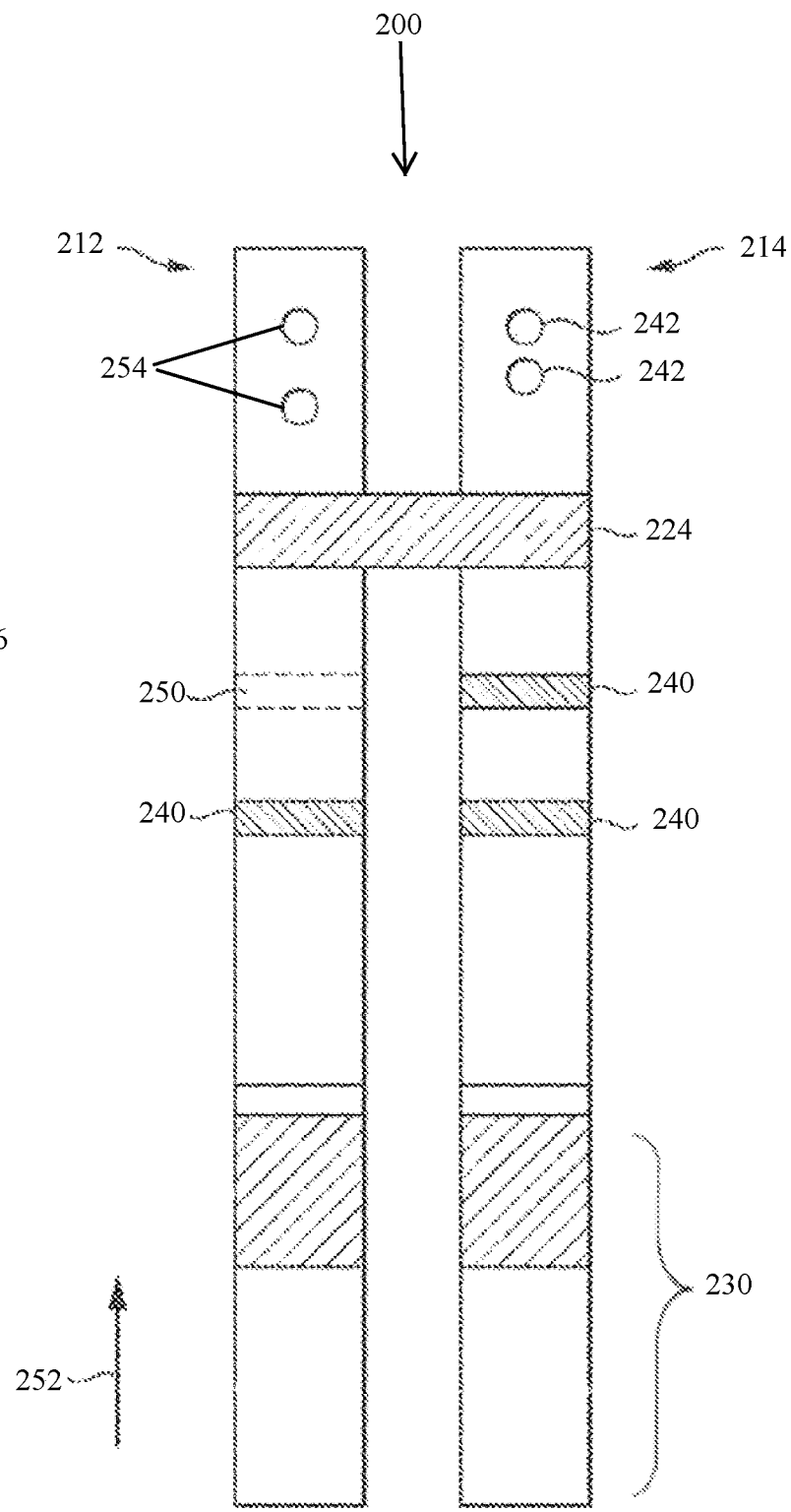
FIG. 6 is a top view of a detecting component in accordance with a second embodiment of the present invention.
Figure 7:
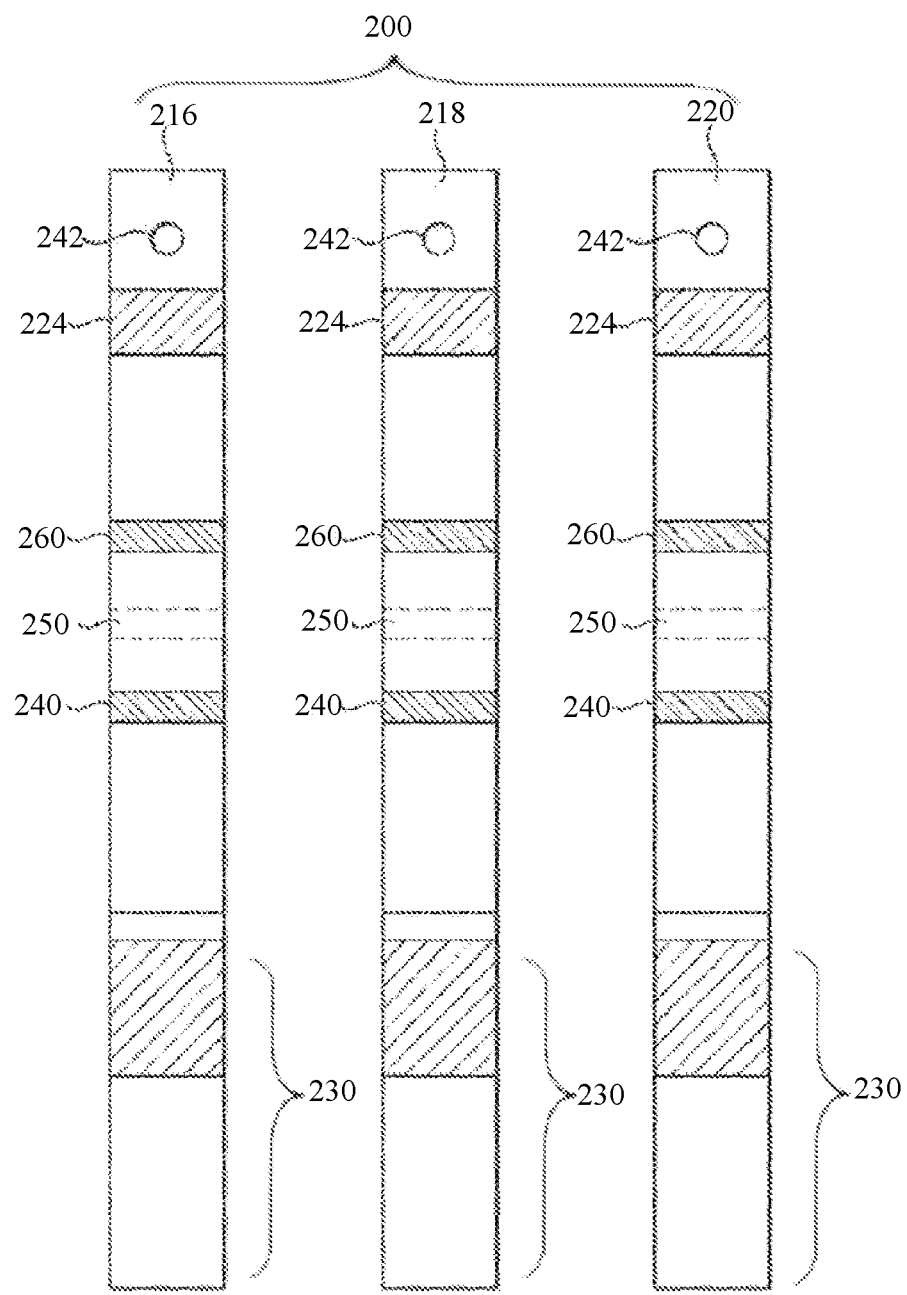
FIG. 7 is a top view of a detecting component in accordance with a third embodiment of the present invention.
Figure 8:
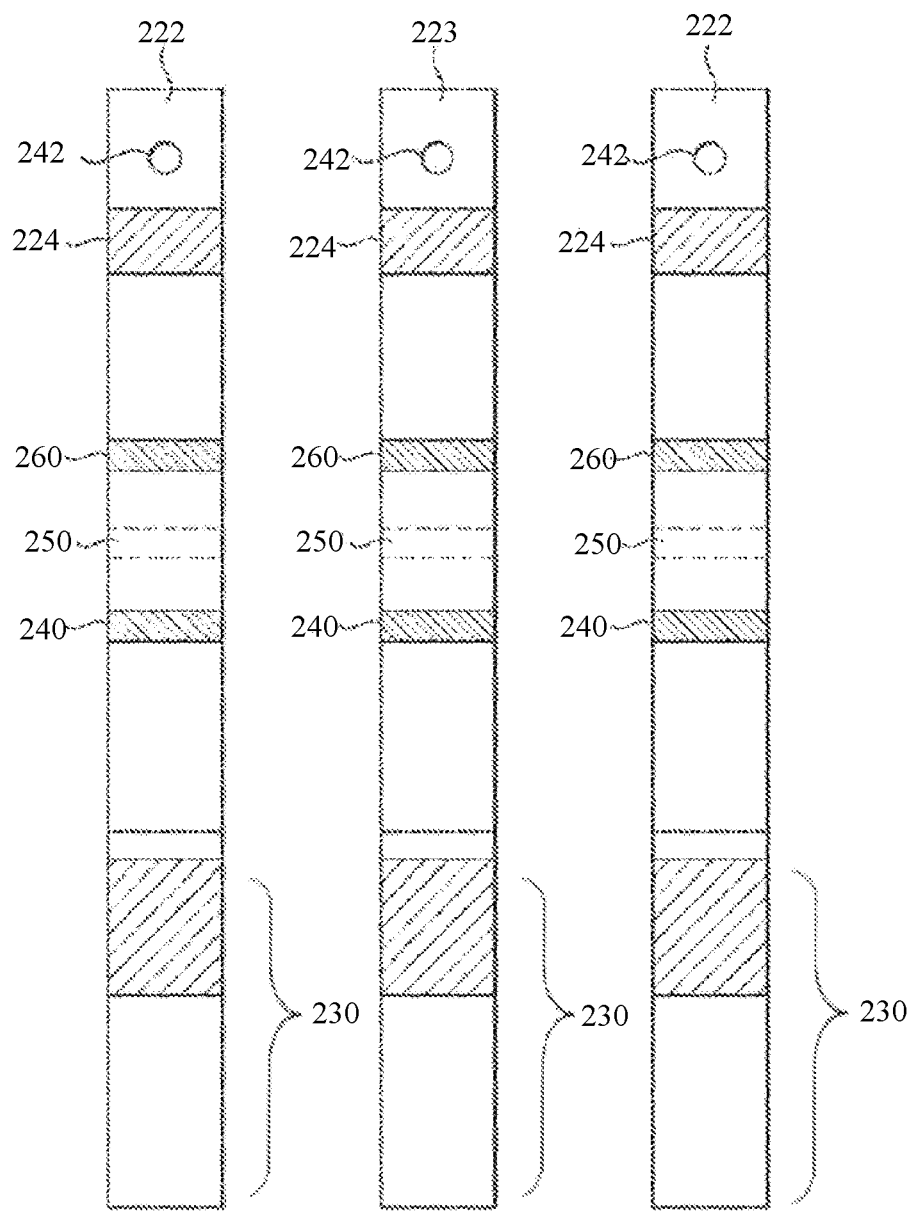
FIG. 8 is a top view of a detecting component in accordance with a fourth embodiment of the present invention.

Urine sample enters assay strips 212, 214 from a common sampling member (not shown) and flows along the strips in the direction indicated by arrow 252 as depicted in FIG. 6. At their proximal ends, that is the end encountered first by a urine sample, both strips have a capture zone 230 that retains, removes, reacts and/or immobilizes anions and both strips 212, 214 are in liquid flow communication with a highly absorbent "sink" 224 towards the distal end, which encourages sample to flow along the assay strips 212, 214. Both strips 212, 214 also comprise, beyond the 'sink' 224, a pair of registration holes 242. These facilitate correct positioning of the strips so that the assay strips 212, 214 can be correctly read by the assay reading components of the device. Note that the pairs of registration holes 254 are not symmetrical, so the strips cannot be inadvertently swapped for each other.

In another embodiment, a separate assay strip is provided for each analyte to be measured or detected. For example, potassium ion is assayed on strip 216, pH (H+) is assayed on strip 218, and sodium is assayed on strip 220. Urine sample is applied to all three assay strips via a common sampling member (not shown). A common 'sink' pad 224 is in liquid flow contact towards the distal end of each assay strip while a common capture pad 230 is adjacent to the common sample application at a proximal end of the assay strips. In this example each assay strip 216, 218, 220 has its own reference zone 250. In addition, each assay strip has a procedural control zone 260, which indicates if the assay has been performed correctly, such as to the extent that the binding reagents have retained their binding properties as is known in the art.

In practice, a urine sample is collected and placed inside a sample container. In one example, the urine sample is cleaned prior to testing. In another example, the sample is analyzed as is. In another example, the sample container is outfitted with a semipermeable membrane that is effective to remove dirt, blood, feces, COVID-19 antigens, COVID-19 antibodies, any other viral material or the like from the urine sample. In another example, the urine sample is collected and placed in contact with an ion detecting strip that is effective to measure sodium ions. In another example, the urine sample is collected and placed in contact with an ion detecting strip that is effective to measure calcium ions. In another example, the urine sample is placed in contact with a chloride detecting strip. In another example, a urine sample is collected and placed in contact with a strip that is partitioned to detect sodium, potassium, and/or calcium ions.

Figure 9:
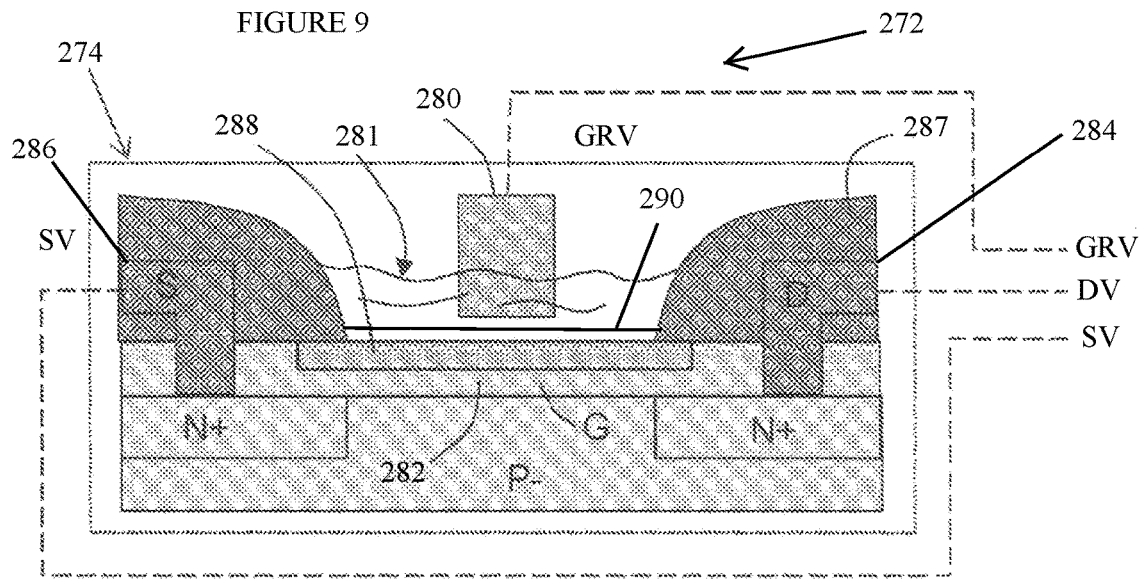
FIG. 9 is a cross-sectional view of a detecting component in accordance with a fifth embodiment of the present invention.

As depicted in FIG. 9, the detecting component 200 can also be configured to include a high sensitivity assay strip 222 for measuring or detecting lower concentrations of ions and/or minerals. The detecting component may also include a low sensitivity assay strip 223 for detecting higher concentrations of ions or minerals. The use of both high and low sensitivity ion assays allow for detection and/or measurement over an extended concentration range. In addition, the use of high and low sensitivity assay strips may also allow quantitative estimation of how long a subject has had COVID-19. For example, one assay strip may be used to test for both high and low concentrations of the same ion. Alternatively, a single assay strip can be partitioned into multiple ion detection zones and used to test for only a high concentration of different ions. Similarly, a single assay strip can be partitioned to detect low concentrations of several different ions. Preparation and/or manufacture of low sensitivity assay strips are known in the art and may include use of low sensitivity reagents or addition of competing reagents that limit the binding of the specific ion of interest.

In another embodiment, the assay strip may include both high and low sensitivity detection zones or portions for urinary sodium to detect and/or measure low and high concentrations of urinary sodium and display a signal and/or color change at the high sensitivity detection zone or portion, for low urinary sodium, while omitting or not displaying a signal and/or color change at the low sensitivity detection zone or portion for high urinary sodium concentrations. Similarly, an assay strip that includes both high and low sensitivity zones or portions for each of urinary potassium, calcium, and/or magnesium may display a signal and/or color change at the low sensitivity detection zone or portion for high urinary ion concentrations, while omitting or not displaying a signal at the high sensitivity detection zone or portion, for low urinary ion concentration, in an effort to detect COVID-19 positive status.

The present invention includes a method of estimating or predicting a COVID-19 infection by collecting a urine sample from an individual followed by performing a first sodium ion urine test of a first sensitivity with a first test strip at a given time on a urine sample; performing a second ion urine test with a second test strip a second time that is at a later time after the first test, and determining a COVID-19 infection is present when the first test on the first test strip is positive and the second test on the second strip is positive. In this method, the test strip is effective to detect and/or quantify a sodium ion concentration that is less than normal or baseline levels of urinary sodium ion, a urinary potassium concentration that is more than normal or baseline levels of urinary potassium, a urinary chloride concentration that is more than normal or baseline levels of urinary chloride ions, and/or urinary pH concentrations that are less than normal or baseline levels of urinary pH for an individual who provided the urine sample.

The method further includes administering the first test at least about 15 minutes, about 30 minutes, about 45 minutes, about 60 minutes, about two hours, about four hours, about 6 hours, 12 hours, about 18 hours, about 24 hours, about 48 hours, or about 72 hours before the second test. In one example, the first test result may indicate a positive initial COVID-19 infection or illness status that is confirmed by a positive second test result. In another example, the test results are helpful to establish normal or baseline urinary ions levels.

The sensitivity of the test device may also have the same degree of sensitivity for each ion or different sensitivities for each ion. The assays of the test device may be on separate lateral flow test strips or separate microfluidic assay flow paths. Alternatively, the assays of the test device may be on the same lateral flow test strip or same microfluidic assay flow path. The tests typically have a sensitivity of more than about 50%, about 60%, about 70% or more than about 80% when practicing the present invention. The method may also include estimating and/or predicting a duration, total duration, age, and/or length of a COVID-19 infection or illness. For example, the levels of detected urinary ions are fed into one or more ML or DL algorithms that are used to estimate the duration, total duration, length, progression, severity, and/or age of COVID-19 infection or illness. By "length" as used herein is meant how long a COVID-19 infection or illness has lasted.

As most ion detecting strips are based on colorimetric techniques, any resulting color change result on the test may be matched to one or more provided color blocks to quantify and/or interpret the results. Alternatively, the resulting color change can be displayed as is through the display window of the testing device, in the form of an indicator band for example, or in combination with one or more LED light displays operated discontinuously. Furthermore, use of one or more dye composition is separately or in combination with colorimetric, electrochemical, precipitation and/or flocculation techniques known to be effective in detecting, measuring, and/or quantifying one or more ions, one or more minerals, or any combinations thereof are non-exhaustive examples in practicing the present invention. Suitable reagents that can be used to detect ions, such as sodium, potassium, chloride, calcium and magnesium, are known to those skilled in the art.

Urinary ions may also be detected using gold nanoparticles (AuNPs) or other nanoparticles modified to give a colorimetric reaction based on ionic concentrations in a sample. Gold nanoparticles (AuNPs) have been widely used as colorimetric probes for metal ions, anions, small molecules, proteins, nucleic acids, and other analytes because of their unique properties. In one example, a probe solution containing AuNPs changes color from red to blue, in the presence of certain ions in a manner that can be observed by the naked eye.

In another example, calcium ions in a sample may detected Tween® 20-modified gold nanoparticles (GNPs), 2-ME/AuNPs, Cysteine/thioglycolate/triethanolamine-modified GNPs, or Calsequestrin-functionalized GNPs, which are effective to quantify varying levels of calcium ions, such as being effective to distinguish between normal or baseline calcium levels and lower than normal levels of calcium ion. In another example, magnesium ions in a sample can be detected using ACEADD-GNR modified gold nanoparticles.

The present invention may include one or more urine test kits containing one or more test strips in communication with or including one or more ion detecting assays embedded therein. Alternatively, the test strips are in communication with one or more ion detecting assays located on a surface of the test strips. The ion detecting assays may be one or more colorimetric assays, one or more enzymatic assays, one or more precipitation assay, one or more flocculation assays, or any combination thereof when practicing the present invention.

The ion detecting assays are generally effective to determine the concentration of or detect the presence of sodium, calcium, potassium, chloride, magnesium, pH, hydrogen ions, hydroxyl ions, bicarbonate, and/or creatinine when practicing the present invention. In one example, a COVID-19 test kit includes a first test strip containing a colorimetric assay or test for sodium ion and a second test strip containing a colorimetric assay or test for potassium ion. The test kit generally has a potassium ion and/or a sodium ion sensitivity of at least about 50%, about 60%, about 70%, about 80%, or more than about 85% when practicing the present invention. The test kit may further include a strip for detection of calcium ions, chloride ions, magnesium ions, hydrogen ions, hydroxyl ions, bicarbonate, or any combination thereof and may have a sensitivity of more than about 50%, 60%, 70%, and more than about 80% when practicing the present invention.

Sodium test (dip) strips, such as those that are available from HOMEHEALTH® (UKI) LTD, Health Mate® Salinity View may also be used to detect the amount of sodium in a urine sample from low (about 0 to about 450 mg/dL) to normal (700-1000 mg/dL) to high (about 1200-1600 mg/dL) in about 60 seconds. Urinary chloride may be detected by urine chloride strips where urinary chloride is measured by reactive strips based on 24 hour samples according to Pannuccio et al (Clin Chem Lab Med 2019 Jul. 26; 57(8): 1162-1168. doi: 10.1515/cclm-2018-1227). Urinary potassium can also be detected using the SALIFERT RTKA Potassium Test Kit that is available on Amazon.com.

Urine samples may also be analyzed by placing the sample in contact with an ion detecting probe. In one example, the ion detecting probe is effective to detect, measure, and quantify urinary ions, such as sodium, calcium, potassium, magnesium, chloride, or any combination of these. Measurement and/or quantification may occur through colorimetric, precipitation, flocculation, and/or electrochemical reactions, and the results through a display in communication with the ion detection probe.

Ion detecting components 200 of the present invention preferably include one or more ion selective electrodes 270 with a specified selectivity for each respective ion of interest. In one embodiment, the ion selective electrode 270 includes an electrochemical sensor 272 in the form of an ion selective field effect transistor 274 such that an ion selective transistor for each respective ion being detected. As depicted in FIG. 9, the ion selective transistor 272 includes a reference electrode 280 and a gate area (G) of a gate electrode 282. The reference electrode 280 may be located on the ion selective transistor 272 at a location proximate the gate area of the gate electrode 282, or optionally located externally from the ion selective transistor 272. The reference electrode 280 is electrically coupled to a gate reference voltage (GRV) that allows for detection or measurement of one or more voltage potentials. The electrochemical sensor 272 also includes a drain electrode 284 coupled to a drain voltage (DV) and a source electrode 286 electrically coupled to a source voltage (SV). A polymeric coating 287, such as an epoxy coating, isolates drain electrode 284 and source electrode 286 from the urine sample 281. The polymeric coating 287 also assists in forming a receptacle in which the urine sample 281 is held opposite the gate electrode 282 without interfering with the substrate of the electrochemical sensor 272. The reference electrode 280 may include a gel electrolyte composition or solution, a metallic compound or composition, a powder, or a solid compound. The reference electrode 280 for the electrolyte composition typically has an exchange wall (not shown) that permits the exchange of ions between the urine sample 281 and the reference electrode electrolyte composition. The exchange of ions between the urine sample and the electrolyte contained in the reference electrode 280 creates a gate trigger voltage at the gate area of gate electrode 282 of the transistor 274 which in turn correlates to the ionic concentration in the urine sample. Similarly, current flow between drain electrode 284 and source electrode 286 may work to amplify detection or measurement of ionic concentration, and thus allow use of current flow and/or the voltages at drain electrodes 284 and source electrodes 286 to determine ionic concentration.

Conventional ion selective transistors, as are known in the art, may include an electronic chip, such as a silicon chip that includes a semiconductive layer typically located on the electronic chip (not shown), and a gate portion (G) located on the semiconductive layer (not shown). When the urine sample is placed in contact with the semiconductive layer, the chip detects and measures a variable voltage potential of the semiconductor layer in contact with one or more ions in the urine sample. The variable voltage potential is positively or inversely proportional to the ion concentration in the urine sample, and the chip is used to quantify the ion concentration.

The use of one or more ion selective membranes 288 is generally positioned proximate the gate area (G) of gate electrode 282 to enable selective passage and quantification of ions/or minerals, as depicted in FIG. 9.

In one embodiment, an ion selective membrane 288 specific to the respective ion of interest is positioned proximate the gate electrode 282 or gate area G to allow direct contact with the urine sample 281, as depicted in FIG. 9. As such, the configuration of the ion selective membrane 288 interposed between the urine sample and gate electrode 282 enables detection and measurement of the ions present in the urine sample. For example, when the ion selective transistor (not shown) is selective to hydrogen ions, the electrochemical sensor is effective to detect or measure the pH of the urine sample which is a function of the hydrogen ion concentration in urine. The pH of the urine sample is measured when a hydrogen sensitive membrane is interposed between the urine sample and the gate portion with the hydrogen sensitive membrane in direct contact with a urine solution. The hydrogen ion sensitive membrane can be the same material as the gate electrode 282 with suitable non-exhaustive examples of semiconductor materials derived from SiO2, Si3N4, Al2O3 or Ta2O5.

Figure 10:
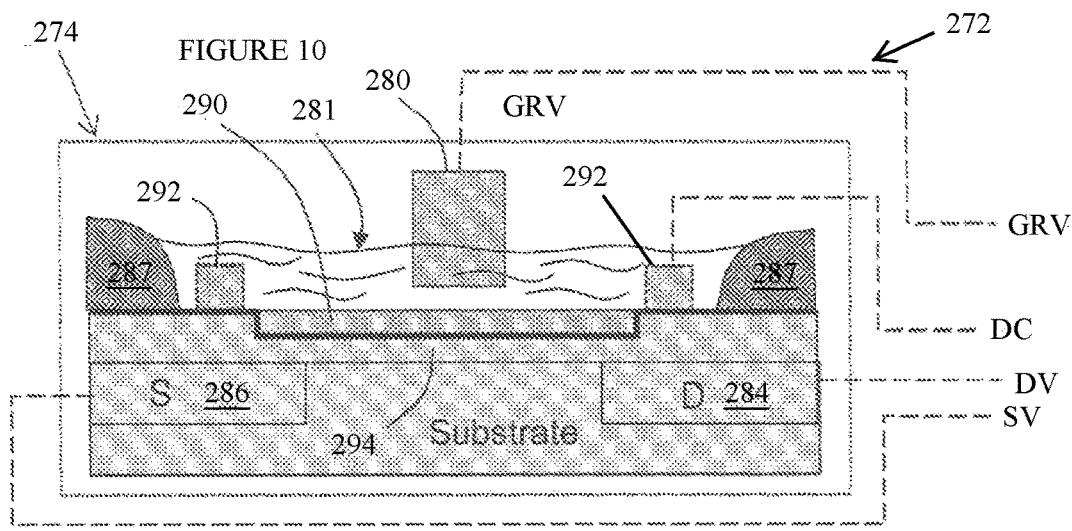
FIG. 10 is a cross-sectional view of a detecting component in accordance with a sixth embodiment of the present invention.

Because ion selectivity is challenging in the presence of competing monovalent and divalent ions, FIG. 9 illustrates use of a filtering composition 290 that filters, retains, reacts with, complexes and/or immobilizes one or more anions, like chloride and hydroxyl ions in the urine sample 281. The filtering composition 290 reacts and/or retains anions to improve selectivity of monovalent and divalent cations that are able to make direct contact with the gate portion 282 of an ion selective electrode 270 specific for the monovalent or divalent cations of interest. Similarly, a polyelectrolyte composition that selectively binds anions present in the urine sample may be used as the filtering composition 290 in accordance with the present invention. The polyelectrolyte composition retains, reacts, complexes or immobilizes anions while allowing cations to make direct contact with the gate area of an ion selective electrode 270 specific for the monovalent or divalent cations to be measured. Further, a first ion selective electrode 292 specific for detection or measurement of one or more anions can be used to quantify anions, as is illustrated in FIG. 10. In this embodiment, the first ion selective electrode 292 enables detection and/or measurement of one or more urinary anions of interest while a cation exchange membrane 290 serves as the filtering composition 290 that allows cations to make direct contact with gate area of a second ion selective electrode 294 specific for cations. This use of the first ion selective electrode 292 and the second ion selective electrode 294 in combination with the filtering composition 290, that retains or hinders the transport of anions while allowing cations to pass through, is believed helpful in improving the selectivity of the ion selective electrode used for detection or measurement of different urinary cations in the presence of competing ions. Similarly, first ion selective electrode 292 is electrically coupled to a voltage (DC) as depicted in FIG. 10.

Figure 11:
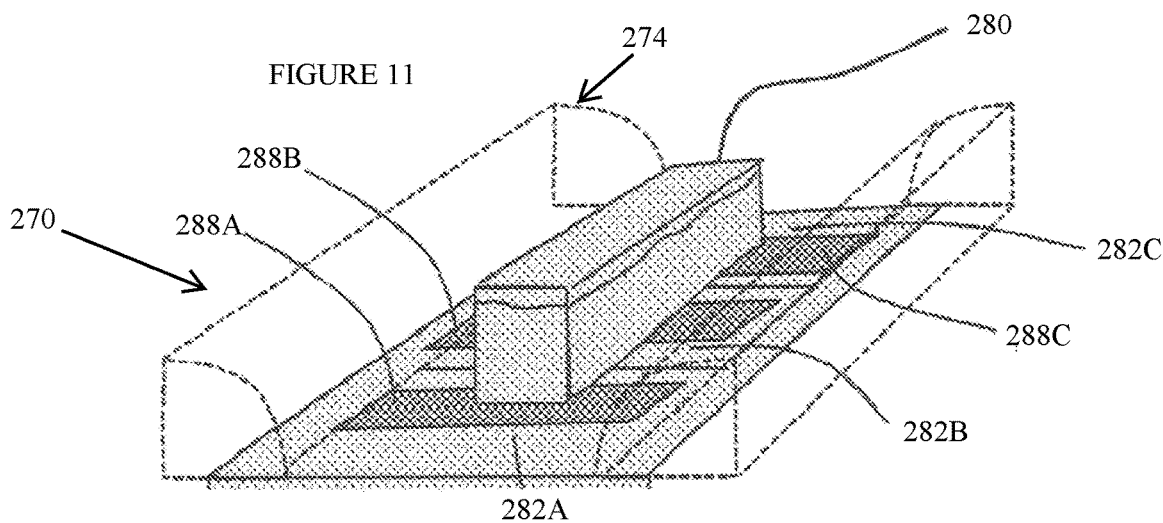
FIG. 11 is a perspective view of a detecting component in accordance with a seventh embodiment of the present invention.

As COVID-19 status is detected by monitoring changing concentrations of multiple urinary ions, the test device can contain two or more ion selective transistors that are effective to measure and/or detect each respective ion. As an example, three ion selective transistors as part of detecting component 200 are depicted in FIG. 11. A first membrane 288*a* in combination with a first electrode 282*a* is used for measuring the concentration of H+ ions to determine pH. A second membrane 288*b* in combination with a second electrode 282*b* is used for measuring the concentration of K+ ions to determine the potassium level. A third membrane 288*c* in combination with a second electrode 282*c* is used for measuring the concentration of Na+ ions to determine sodium level. Preferably, the aforementioned concentration measuring occurs after the filtering, retention, immobilization and/or hindering transport of urinary anions by a filtering composition (not shown).

AuNPs can also be combined with ion detection probes to form ion detection devices that are effective to determine an ionic concentration in a urine sample and render results in good agreement with a second ion or mineral concentration technique, such as atomic absorption spectroscopy (AAS).

An example of a device that can detect chloride in a urine sample includes the Oakton by Cole-Parmer® Combination Ion-Selective Electrode (ISE), Chloride (CI) that is available from Cole Parmer. Furthermore, this device can be fitted to a pH meter to allow both quantification of pH and chloride concentrations in a urine sample.

Returning to FIG. 2, the analyzing component 300 of the testing device 100 analyzes one or more results o readings of the detecting component 200 to determine COVID-19 status. The analyzing component 300 calculates and compares the difference between one or more results or readings, and one or more baseline values, one or more threshold values, or one or more stored results. The analyzing component 300 can also process one or more results by analysis through one or more algorithms electronically coupled to the analyzing component 300. The analyzing component 300 can be electronically coupled to one or more wireless enabled devices (not shown), one or more remote computing devices (not shown), one or more portable electronic devices (not shown) including, but not limited to, a smartphone, PDA, computer, an app, laptop, cloud server, or any other wireless enabled device that can send or receive data through a wireless link 112.

In addition, the test device 100 is in communication with an analyzing component 300 or analyzing system 300 that is effective to calculate, estimate, predict, quantify, analyze or read one or more urinary ion assay results. The system 300 may include one or more look up tables, microprocessors, application-specific integrated circuits (ASICs), computerized control systems, or any combination thereof, to facilitate processing and interpretation of ion testing results. The system 300 may be located on the test device 100 or located externally from the test device 100, such as located on a cloud server, in an app or the like.

When the testing device 100 includes one or more assay strips 200, the testing device 100 measures a change in color or signal responsive to the amount of analyte of interest. The analytes are detected and read by the analyzing component 300 of the test device 100. Current detected or measured readings or results can be displayed through the display window 118 as a color change, an indicator band, or digital display onto an external screen electronically connected to the analyzing component 300 through wireless link 112.

The display component 400 may include one or more LED lights corresponding to one or more status indicators. In one embodiment, the display component 400 includes a first status indicator and a second status indicator corresponding to positive and negative COVID-19 status, respectively. In another embodiment, the display component 400 includes a first status indicator, a second status indicator and a third status indicator corresponding to positive, negative and unknown COVID-19 status, respectively as is known in the art. In another embodiment, the display component 400 includes green, yellow and red LED lights on the display that are operated discontinuously in response to a COVID-19 status.

The test device 100 may also include the display component 400 that is effective to help calculate, quantify, predict, estimate, evaluate, analyze and/or display one or more assay results, and/or one or more outcomes to a user. The test device 100 may be adapted and configured to display an approximate COVID-19 infection and/or illness age, duration, total duration, length, progress, and/or severity calculated for a urine sample or individual. The age, duration, total duration, length, progress, and/or severity of the COVID-19 infection and/or illness may be outputted in intervals of minutes, hours, days, weeks, or months. For example, the duration output may be 24 hours. In another example, the length output might be two weeks.

As noted, urinary ionic and/or mineral levels or concentrations may also be monitored at specified time intervals for a specific length of time in an amount that is sufficient to establish normal or baseline values to help analyze or interpret test device data. For example, daily sodium, potassium, chloride, blood pressure, pH and/or temperature values may be recorded and prove helpful in establishing baseline values. In another example, urinary sodium, potassium, chloride, blood pressure, pH and/or temperature values may be monitored or recorded every 15, 30, 45, 60, 2 hours, 4 hours, 6 hours, 12 hours, 24 hours, or 48 hours in order collect data suitable for training one or more algorithms to estimate or predict COVID-19 infection and/or illness result or status. In another example, daily urinary sodium, pH potassium, calcium, and chloride levels along with blood pressure may be monitored for at least 3 days and used to estimate or predict a COVID-19 infection. In another example, daily body temperature, blood pressure, and urinary potassium, chloride, pH and creatinine values are measured, recorded for at least seven days and used to determine a COVID-19 infection status. In another example, urinary sodium, potassium, calcium, chloride and magnesium levels, urinary pH, blood pressure and creatinine data are measured, recorded for at least one time and may be used to estimate or predict a COVID-19 infection.

The test device 100 may also contain a memory component 500 in the form of a digital memory device programmed with at least one predetermined ion value or ion threshold for each ion that is being measured. Alternatively, the digital memory device is programmed with at least one ion value or ion threshold that represents the difference between two or more urinary ion values. In another example, the digital memory device is programmed with one or more algorithms that are effective to interpret one or more urinary ion values, the difference between two or more urinary ion values, and/or one or more results, outcomes, statuses produced by the test device. When the digital memory device is programmed with one or more algorithms, the digital memory device is in electronic communication with the algorithms that are effective to process urinary ion, creatine, pH, body temperature, blood pressure, or mineral data, and produce and/or translate the results into a positive or negative, or unknown COVID-19 infection or illness.

The digital memory device of the test device 100 may also include a microprocessor, an application-specific integrated circuit, or other programmable computer control system that is programmed with one or more algorithms that are effective to process, analyze, and/or evaluate urinary ion, mineral, and/or pH data. For example, the algorithm is effective to process urinary ion, mineral, pH, and/or creatine data by comparing the detected, measured and/or monitored data with predetermined thresholds. In another example, the algorithm is effective to process urinary ion, mineral, pH and/or creatine data by comparing a difference between two or more values obtained by, stored, and/or made accessible to the test device. In another example, the algorithms are effective to process temperature, blood pressure, urinary ion, pH, mineral and/or creatine data, and to classify or interpret the results as positive, negative, or unknown COVID-19 infection or illness status.

The test device 100 is generally effective to interpret at least one ion assay test result and is effective to display at least one test result to a user. The test device 100 may include one or more light sources to illuminate one or more microfluidics assay detection zones, one or more lateral flow assay detection zones, or any combination thereof along with one or more photodetectors that detect light reflected or transmitted by the detection zones. For example, the detection zones can be illuminated to a red, yellow, or green zone, color or light that corresponds to positive, unknown, or positive negative COVID-19 infection or illness status. In another example, the detection zones are illuminated to a red or green zone, color or light that corresponds to a positive or negative COVID-19 infection or illness status. In operation, the LED lights are operated discontinuously and in response to the detected and analyzed results [analytes] in a urine sample. The remote computing device may also optionally include a time chart showing the evolution of analytes over time when practicing the present invention.

Suitable test devices of the present invention include devices that are effective to quantify a sodium ion concentration that ranges from less than about 20 mEq/L to more than about 220 mEq/L; a potassium ion concentration that ranges from less than about 20 mEq/L to more than about 220 mEq/L; a calcium ion concentration that ranges from less than about 50 mg to more than about 150 mg; a chloride ion concentration that ranges from less than about 20 mEq/L to more than about 220 mEq/L; a magnesium ion concentration that ranges from less than about 50 mg to more than about 300 mg; a creatinine concentration that ranges from less than about 100 mg to more than about 3000 mg and/or less than about 10 mg/dl to more than about 400 mg/dl per day; a specific gravity of about 0.8 to about 1.5; and/or pH values that range from about 1 to about 14.

Non exhaustive suitable urine analyzers for determining the pH of a urine sample include Siemens® 2161 Multistix® 10 SG Reagent Strips for Urinalysis and the FL-401 PRECISION™ Urine Analyzer. The FL-401 PRECISION™ Urine Analyzer measures and records specific gravity, pH, urinary calcium, creatinine, and other urine analytes in combination with one or more reagent strips, such as the URS-10T Urinalysis Reagent Strips 10 panel.

Ions in urine samples may also be detected using a smartphone-based colorimetric sensor in electronic communication with a machine learning (ML) or deep learning (DL) algorithm that is executed to detect, measure, and/or quantify one or more color changes when practicing the present invention. In an example, when one or more ions, or one or more minerals, or any combinations thereof, are brought into contact with a mixture or solution of functionalized gold nanoparticles, the mixture or solution will change from a first color to a second color. In one example, the mixture or solution may change from a red color to a purple color in a manner that is proportional to each ion concentration and/or combined ion concentration in contact with the gold nanoparticles. In a second example, the mixture may change from a red color to a blue color in a manner that is proportional to each ion concentration and/or combined ion concentration in contact with the gold nanoparticles. The smartphone camera is turned on and used to capture any color changes in one or more images that may be processed by one or more ML and/or DL algorithms. The ML and/or DL algorithms have been trained on data to correlate color change and/or colors captured or embedded in each image or pixel to enable prediction of an ionic concentration in a urine sample. In another example, pH, blood pressure and/or body temperature values are used with image and/or color data and fed into ML and/or DL models to enable detection, measurement and/or quantification of ionic concentration.

The test device 100 may be programmed with a lower sodium ion threshold and an upper sodium ion threshold. When the test device 100 is programmed with a lower sodium ion threshold and an upper sodium threshold, a detected, measured and/or quantified sodium ion value from the test device 100 that is lower than the lower sodium ion threshold may indicate a COVID infection and/or illness is present. Alternatively, if a detected, measured, and/or quantified sodium ion value higher than the upper sodium ion threshold programmed on the test device 100 may indicate a COVID infection and/or illness is not present. If the detected, measured, and/or monitored sodium value result falls between the lower threshold and the upper threshold, the test device may output a classification status as unknown. Furthermore, an unknown COVID-19 infection or illness status in a first test result may subsequently be classified as either a positive or a negative status after performing a second or additional tests on additional urinary samples. In another example, if the detected, measured, and/or monitored sodium value result falls between the lower threshold and the upper threshold, an indication of a positive or negative COVID-19 status or result, instead of an unknown status, may be estimated or predicted by evaluating potassium, calcium, hydrogen, hydroxyl, pH and/or chloride ion urinary assay results or data along with the sodium value.

The test device 100 may be programmed with a lower potassium ion threshold and an upper potassium ion threshold. When the test device 100 is programmed with a lower and an upper potassium ion threshold value, a detected, measured, and/or monitored potassium ion value from the test device that is lower or below the lower threshold may indicate a COVID-19 infection and/or illness is not present. Alternatively, a detected, measured and/or monitored potassium ion value or result that is above or greater than the upper potassium ion threshold may indicate a COVID-19 and/or illness is present. If the detected, measured, and/or monitored potassium value result falls between the lower threshold and the upper threshold, the test device may output a classification status as unknown. If the detected, measured, and/or monitored potassium value result falls between the lower threshold and the upper threshold, an indication of a positive or negative COVID-19 status or result, instead of an unknown status, may be estimated or predicted by evaluating sodium, calcium, hydrogen, hydroxyl, pH and/or chloride ion urinary assay results or data along with the potassium value.

The test device 100 may also be programmed with a lower chloride ion threshold and an upper chloride ion threshold. When the test device 100 is programmed with a lower and an upper chloride ion threshold value, a detected, measured, and/or monitored chloride ion value from the test device that is lower or below the lower threshold may indicate a COVID-19 infection and/or illness is not present. Alternatively, a detected, measured and/or monitored chloride ion value or result that is above or greater than the upper chloride ion threshold may indicate a COVID-19 and/or illness is present. If the detected, measured, and/or monitored chloride value result falls between the lower threshold and the upper threshold, the test device may output a classification status as unknown. If the detected, measured, and/or monitored chloride value result falls between the lower threshold and the upper threshold, an indication of a positive or negative COVID-19 status or result, instead of an unknown status, may be estimated or predicted by evaluating potassium, calcium, hydrogen, hydroxyl, pH and/or sodium ion urinary assay results or data along with the chloride value or by evaluating additional urinary samples taken at a later time.

The test device 100 may be programmed with a lower calcium ion threshold and an upper calcium ion threshold. When the test device 100 is programmed with a lower and an upper calcium ion threshold value, a detected, measured, and/or monitored calcium ion value from the test device that is lower or below the lower threshold may indicate a COVID-19 infection and/or illness is not present. Alternatively, a detected, measured and/or monitored chloride ion value or result that is above or greater than the upper calcium ion threshold may indicate a COVID-19 and/or illness is present.

If the detected, measured, and/or monitored calcium value result falls between the lower threshold and the upper threshold, the test device may output a classification status as unknown. If the detected, measured, and/or monitored calcium value result falls between the lower threshold and the upper threshold, an indication of a positive or negative COVID-19 status or result, instead of an unknown status, may be estimated or predicted by evaluating potassium, sodium, hydrogen, hydroxyl, pH and/or chloride ion urinary assay results or data along with the calcium value. If the detected, measured, and/or monitored calcium value or result is between the lower threshold and the upper threshold, this may indicate that a COVID infection is or is not present, and may result in the test device outputting an unknown COVID-19 infection or illness result in the present invention. If the detected, measured, and/or monitored calcium value result falls between the lower threshold and the upper threshold, an indication of a positive or negative COVID-19 status or result may be calculated by incorporating sodium, chloride, hydrogen, hydroxyl, pH and/or potassium ion assay results or data, and estimating or predicting COVID-19 infection or illness status from the combination of this data or by evaluating additional urinary samples taken at a later time.

The test device 100 may be programmed with a lower magnesium ion threshold and an upper magnesium ion threshold. When the test device is programmed with a lower and an upper magnesium ion threshold value, a detected, measured, and/or monitored magnesium ion value from the test device that is lower or below the lower threshold may indicate a COVID-19 infection and/or illness is not present. Alternatively, a detected, measured and/or monitored magnesium ion value or result that is above or greater than the upper magnesium ion threshold may indicate a COVID-19 and/or illness is present. If the detected, measured, and/or monitored magnesium value result falls between the lower threshold and the upper threshold, the test device may output a classification status as unknown. If the detected, measured, and/or monitored magnesium value result falls between the lower threshold and the upper threshold, an indication of a positive or negative COVID-19 status or result, instead of an unknown status, may be estimated or predicted by evaluating potassium, calcium, hydrogen, hydroxyl, pH and/or chloride ion urinary assay results or data along with the magnesium value, or by evaluating additional urinary samples taken at a later time.

The test device 100 may also include a control function to indicate if the device is functionally correctly or has functioned correctly. The test device 100 may be a point-of-care device or a test device that is disposed of after a single use.

The test device 100 may include a disposable visually-reading device combined with a separate durable assay reading device, such that the separate durable assay reading device comprises a camera, a smart phone or other digital hand-held reading device.

In general, one or more artificial intelligence algorithms, such as one or more ML algorithms, one or more DL algorithms, or any combination of these, can be trained using sodium, potassium, chloride, calcium, and/or magnesium data, pH, creatinine, blood pressure, body temperature and/or specific gravity data to create one more ML and/or DL models effective to estimate or predict COVID-19 infection or illness status, duration, total duration, length, severity, and/or age when practicing the present invention.

For example, a dataset from one or more individuals based on a timeframe of one or more days, similar to that which is presented in TABLE 1A and 1B, can be used to train an ML classifier and/or regressor in order to estimate or predict COVID-19 infection or illness status as well as infection length, age, duration and/or total duration in the present invention.

The present invention may typically include running or executing one or more ML and/or DL models that have been trained with ionic and/or mineral data and are effective to analyze, interpret and/or enable estimation and/or prediction of COVID-19 infection or and/or illness status, age, duration, severity and/or total duration.

In an example, data from at least 1 day, 3 days, 5 days, 10 days, 15 days, 20 days, or 31 days can be used as normal or baseline urinary values to train a ML model, such as a gradient boosting classifier. In another example, data from at least 1 hours, 2 hours, 4 hours, 6 hours, 12 hours, 24 hours, 3 days, 5 days, 7 days, 18 days, or 15 days of a COVID-infection can also be used to train an ML model, such as a gradient boosting classifier.

While the data in Table 1A, 1B and 2 are presented in different tables, both "normal" and "COVID-19 infection" data can be combined into one dataset and used for training, testing, validation, estimation, and prediction of COVID-19 infection or illness status. Table 3 is an example of a dataset suitable for training one or more ML and/or DL models.

ML algorithms generally include logistic regression, linear regression, naïve bayes classifier, random forest, support vector machine, decision tree, gradient boosting regressor, gradient boosting classifier, or the like. Data is typically split into training and test samples prior to feeding (inputting) into one or more ML and/or DL algorithms.

Alternatively, a deep learning neural network known as a convolutional neural network, or ConvNet, can be used to tell how much ion concentration, such as how much sodium, potassium, chloride, etc., may be present in a urine sample based on the one or more pixels captured by the smartphone camera. Additional examples of DL models include recurrent neural networks, CNN, LSTM and/or combinations thereof.

In an example, when urinary potassium and chloride levels greater than or higher than normal or baseline urinary values, and urinary pH values lower than normal or baseline urinary pH values are inputted into one or more ML models of the present invention that are trained to predict COVID-19 infection or illness status, a positive COVID-19 infection status or illness was predicted, displayed, and recorded. In another example, a positive COVID-19 infection status or illness may be estimated or predicted when urinary sodium, potassium and chloride levels greater than normal urinary values, and urinary pH values lower than normal urinary pH values are inputted into one or more ML models of the present invention that are trained to predict a COVID-19 infection or illness. In another example, a positive COVID-19 infection status or illness may be estimated or predicted when urinary calcium, potassium and chloride levels greater than normal urinary values, and urinary pH values lower than normal urinary pH values are inputted into one or more ML models of the present invention that are trained to predict a COVID-19 infection or illness. In another example, a positive COVID-19 status or illness may be predicted when urinary magnesium, potassium and chloride levels greater than normal urinary values, and urinary pH values lower than normal urinary pH values are fed into one or more ML models of the present invention that are trained to predict a COVID-19 infection or illness.

A negative COVID-19 infection status or illness may be predicted when urinary potassium and chloride levels lesser than or within normal urinary values, and normal urinary pH values are fed into one or more ML models of the present invention that are trained to predict a COVID-19 infection or illness. A negative COVID-19 infection status or illness may also be predicted when urinary sodium, potassium, and chloride levels lesser than or within normal urinary values, and normal urinary pH values are inputted into one or more ML models of the present invention that are trained to predict a COVID-19 infection or illness. A negative COVID-19 infection status or illness may also be predicted when urinary calcium, potassium, and chloride levels lesser than or within normal urinary values, and normal urinary pH values are fed into one or more ML models of the present invention that are trained to predict a COVID-19 infection or illness.

A first unknown COVID-19 infection status or illness may be predicted when urinary sodium, potassium and chloride levels lesser than or within normal urinary values, and normal urinary pH values are fed into one or more ML models of the present invention that are trained to predict a COVID-19 infection or illness. A second negative COVID-19 infection or illness status may be predicted should second or additional urinary test results with similar urinary sodium, potassium and chloride levels lesser than or within normal urinary values along with normal urinary pH values are evaluated using one or more ML models of the present invention that are trained to predict a COVID-19 infection or illness.

A first unknown COVID-19 infection status or illness may be predicted when normal urinary pH values, urinary potassium, and chloride levels greater than normal urinary values, and urinary sodium values that are less than normal urinary sodium values are evaluated by one or more ML models of the present invention that are trained to predict a COVID-19 infection or illness. A second positive COVID-19 infection or illness status may be predicted should second or additional urinary test results collected within or after a 2-hour timeframe based on similar normal urinary pH values, urinary potassium, and chloride levels greater than normal urinary values, and urinary sodium values that are less than normal urinary sodium values are evaluated using the ML models of the present invention that are trained to predict a COVID-19 infection or illness.

It is recognized there are multiple variations beyond what are outlined in the detailed description to accomplish the objectives set forth by the current invention. Further alternative embodiments provide additional utility of the device for the convenience of the user. As such, although the present invention has been described with reference to preferred and alternative embodiments, workers skilled in the art will recognize that changes may be made in form and detail without departing from the spirit and scope of the invention.

The invention claimed is:

1. A method of producing a COVID-19 infection result status of a subject utilizing a urine sample, the method comprising:
   contacting a first urine sample with an ion detecting probe to obtain a first sodium ion concentration and a first potassium ion concentration;
   contacting a second urine sample with the ion detecting probe to obtain second sodium ion concentration and a second potassium ion concentration;

producing a COVID-19 status by comparing the second sodium ion concentration and the second potassium ion concentration to respective first sodium ion concentration and first potassium ion concentration, wherein a positive COVID-19 status is produced when the second sodium ion concentration is lower than the first sodium ion concentration and the second potassium ion concentration is higher than the first potassium ion concentration and wherein the first sodium ion concentration ranges from 40 mEq/L to 220 mEq/L and the first potassium ion concentration ranges from 25 mEq/L to 125 mEq/L.

2. The method of claim 1 wherein the second sodium ion concentration is at least 5% less than the first sodium ion concentration.

3. The method of claim 1 wherein the second potassium ion concentration level is at least 10% more than the first potassium ion concentration.

4. A method of producing a COVID-19 infection status in a subject utilizing a urine sample, the method comprising:
 contacting the urine sample with an ion detecting component to detect a potassium ion level;
 measuring a pH level of the urine sample with the ion detecting component, wherein a COVID-19 positive status is produced when the detected potassium ion level is higher than a threshold potassium ion concentration and the measured pH level is lower than a threshold pH concentration and wherein the threshold pH concentration ranges from 4.5 to 8.

5. The method of claim 4 wherein the measured pH level is at least 10% lower than the threshold pH concentration.

6. The method of claim 4 wherein a COVID-19 positive status is produced by measuring a chloride ion level with the ion detecting component, wherein the measured chloride ion level is at least 10% higher than a threshold chloride concentration.

7. The method of claim 6 wherein the threshold chloride concentration ranges from 110 mEq per Liter to 250 mEq per Liter.

8. A test device for detecting ions in a urine sample, the test device comprising:
 a housing having a urine reception area and a urine analyzing area;
 a sample application zone extending from the housing;
 a detecting component to detect a concentration of a first ion in the urine sample via a capture zone in communication with the sample application zone, the detecting component in liquid communication with the sample application zone, wherein the capture zone has a filter that filters out at least one anion from the urine sample while allowing at least one cation to be detected in a detection zone;
 a microprocessor analyzer enclosed in the housing that analyzes at least one quantified result from the detecting component.

9. The test device of claim 8 and further comprising a display component in communication with the microprocessor analyzer, wherein the display component includes at least one indicator band or at least one color component.

10. The test device of claim 8 wherein the capture zone comprises sulfonic acid resides.

11. The test device of claim 8 wherein the ion detecting component is an ion detecting strip containing a first ion detecting zone and a second ion detecting zone.

12. The test device of claim 11 wherein the first ion detecting zone and the second ion detecting zone each include a first ion sensitivity area and a second ion sensitivity area.

13. The test device of claim 8 wherein the ion detecting component is an ion detecting strip, the ion detecting strip containing a first ion sensitivity zone for detecting a first sodium ion concentration, and a second ion sensitivity zone for detecting a second sodium ion concentration.

14. The test device of claim 8 wherein the display component displays a positive, unknown or negative result status.

15. A test device for detecting ions in a urine sample, the test device comprising:
 a housing having a urine reception area and a urine analyzing area;
 a detecting component contained within the housing to detect the concentration of at least one ion in the urine sample, wherein the detecting component comprises:
  a first ion selective electrode;
  a first ion sensitive membrane; and
  a second ion selective electrode, wherein the first ion sensitive membrane is interposed between the urine sample and the second ion selective electrode; and
  a microprocessor analyzer contained within the housing that analyzes at least one quantified result from the detecting component, wherein the first ion sensitive membrane is a cation sensitive membrane that allows at least one cation to pass through and wherein the first ion selective electrode quantifies urinary sodium ion.

16. The test device of claim 15 wherein the second ion selective electrode quantifies urinary potassium ion.

17. The test device of claim 15 wherein the second ion selective electrode quantifies urinary calcium ion.

18. The test device of claim 15 wherein the second ion selective electrode quantifies urinary magnesium ion.

* * * * *